United States Patent
Model et al.

(10) Patent No.: US 11,337,681 B2
(45) Date of Patent: May 24, 2022

(54) WEARABLE FLUIDIC DEVICE AND SYSTEM FOR SWEAT COLLECTION AND EXTRACTION

(71) Applicant: Epicore Biosystems, Inc., Cambridge, MA (US)

(72) Inventors: Jeffrey B. Model, Cambridge, MA (US); Roozbeh Ghaffari, Cambridge, MA (US); Alexander J. Aranyosi, Medford, MA (US); Stephen P. Lee, Ann Arbor, MI (US); Milan S. Raj, Natick, MA (US)

(73) Assignee: Epicore Biosystems, Inc., Cambridge, MA (US)

(*) Notice: Subject to any disclaimer, the term of this patent is extended or adjusted under 35 U.S.C. 154(b) by 7 days.

(21) Appl. No.: 16/758,590

(22) PCT Filed: Nov. 21, 2018

(86) PCT No.: PCT/US2018/062178
§ 371 (c)(1),
(2) Date: Apr. 23, 2020

(87) PCT Pub. No.: WO2019/104118
PCT Pub. Date: May 31, 2019

(65) Prior Publication Data
US 2021/0186470 A1    Jun. 24, 2021

Related U.S. Application Data

(60) Provisional application No. 62/589,702, filed on Nov. 22, 2017.

(51) Int. Cl.
*A61B 10/00* (2006.01)
*A61B 5/01* (2006.01)
(Continued)

(52) U.S. Cl.
CPC ............ *A61B 10/0064* (2013.01); *A61B 5/01* (2013.01); *A61B 5/1455* (2013.01);
(Continued)

(58) Field of Classification Search
CPC .............. A61B 5/4266; A61B 5/14517; A61B 10/0064
See application file for complete search history.

(56) References Cited

U.S. PATENT DOCUMENTS

| 4,542,751 A | 9/1985 | Webster et al. |
| 4,635,488 A | 1/1987 | Kremer |

(Continued)

FOREIGN PATENT DOCUMENTS

WO    2018223058 A1    12/2018

OTHER PUBLICATIONS

International Search Report, Application No. PCT/US2018/062178, dated Feb. 1, 2019.
(Continued)

*Primary Examiner* — Daniel L Cerioni
*Assistant Examiner* — Raymond P Dulman
(74) *Attorney, Agent, or Firm* — MacMillan, Sobanski & Todd, LLC

(57) ABSTRACT

A sweat collection device includes a flexible body having a first, outwardly facing surface and a second, skin-facing surface, and a sweat collection channel formed in the body, the sweat collection channel having a first end defining a sweat inlet port, and a second end defining a sweat outlet port. The sweat inlet port and the sweat outlet port are configured to be closed and sealed such that the sweat collection device and the collected sweat therein may be stored and shipped.

11 Claims, 13 Drawing Sheets

(51) Int. Cl.
  *A61B 5/145* (2006.01)
  *A61B 5/1455* (2006.01)
  *A61B 5/00* (2006.01)

(52) U.S. Cl.
  CPC ...... *A61B 5/14517* (2013.01); *A61B 5/14532* (2013.01); *A61B 5/14539* (2013.01); *A61B 5/14546* (2013.01); *A61B 5/4266* (2013.01); *A61B 5/743* (2013.01); *A61B 5/4875* (2013.01)

(56) References Cited

U.S. PATENT DOCUMENTS

| | | | | |
|---|---|---|---|---|
| 2007/0156106 | A1* | 7/2007 | Klofta | A61F 13/42 604/361 |
| 2010/0063372 | A1* | 3/2010 | Potts | A61B 5/14521 600/346 |
| 2010/0132485 | A1* | 6/2010 | Erez | A61B 5/4266 73/863.11 |
| 2011/0275918 | A1* | 11/2011 | Yamashita | A61B 5/14521 600/345 |
| 2014/0276220 | A1* | 9/2014 | Briscoe | A61B 5/6831 600/580 |
| 2014/0323819 | A1* | 10/2014 | Hyde | A61B 5/01 600/301 |
| 2017/0119289 | A1* | 5/2017 | Yoshioka | A61B 5/1455 |
| 2017/0296114 | A1 | 10/2017 | Ghaffari et al. | |
| 2018/0020966 | A1* | 1/2018 | Begtrup | A61B 5/01 600/301 |
| 2018/0064377 | A1* | 3/2018 | Rogers | A61B 5/14517 |
| 2019/0246959 | A1* | 8/2019 | Ionescu | A61B 5/1477 |
| 2020/0093416 | A1* | 3/2020 | Rogers | A61B 5/14539 |

OTHER PUBLICATIONS

Koh et al., "A soft, wearable microfluidic device for the capture, storage, and colorimetric sensing of sweat", Science Translational Medicine, 2016, vol. 8, pp. 1-13.
The Extended European Search Report, Application No. 18881519.5, dated Jul. 19, 2021.

* cited by examiner

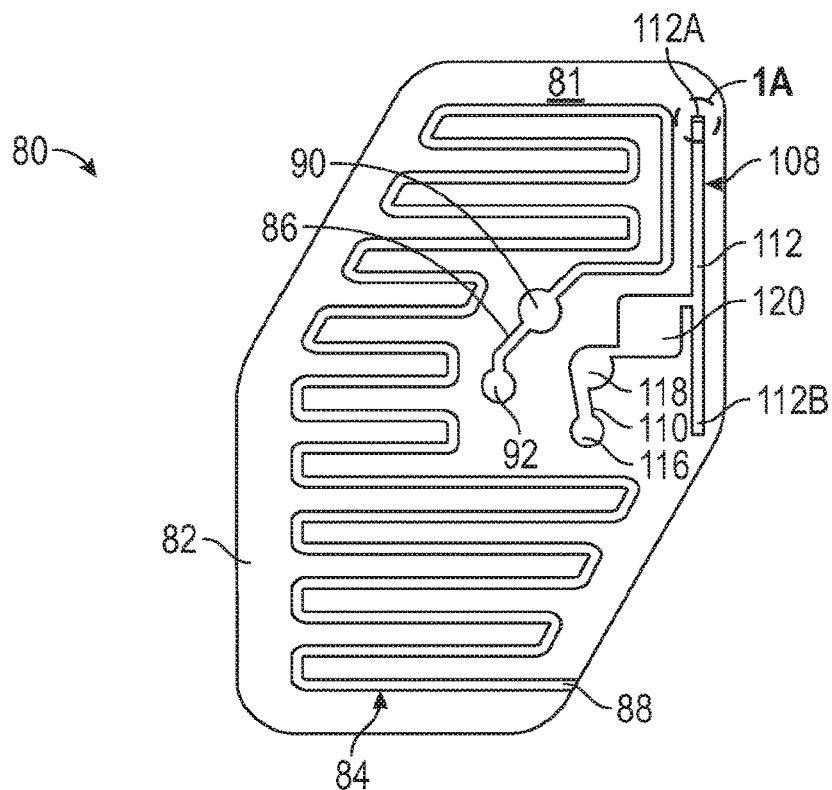 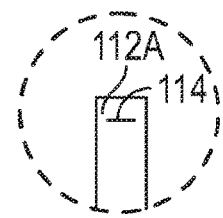
FIG. 1  FIG. 1A
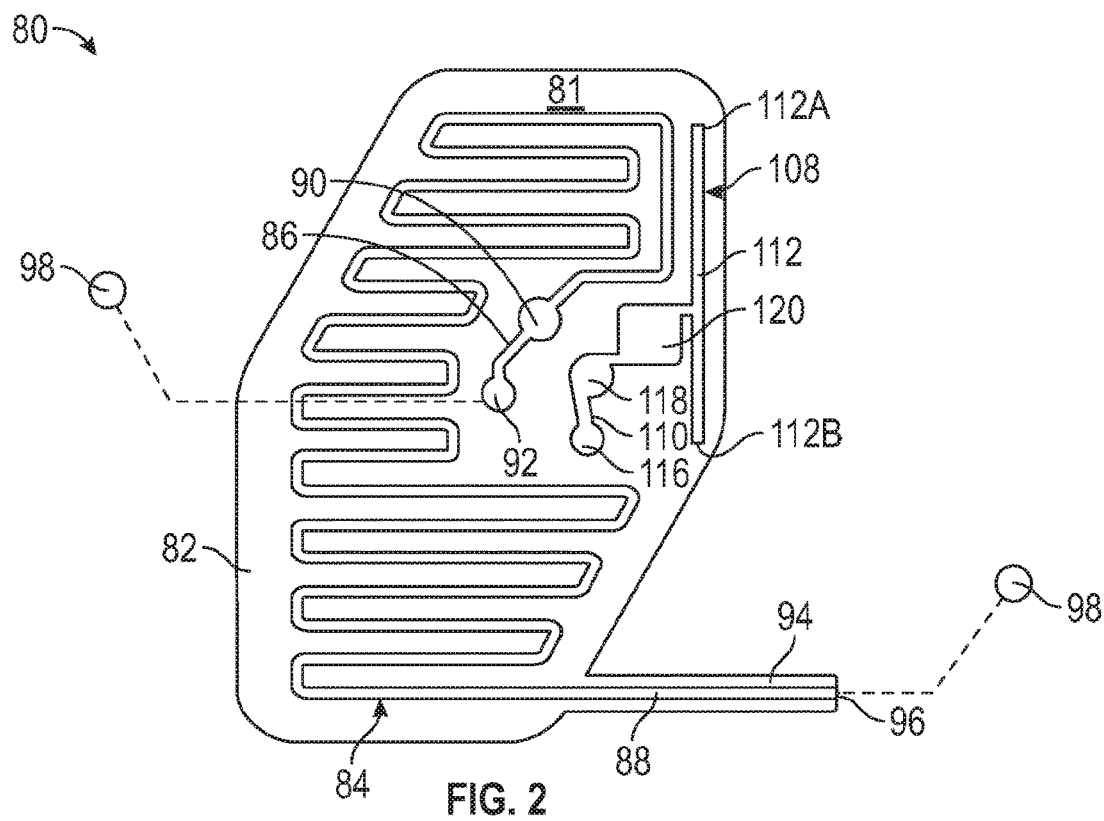
FIG. 2

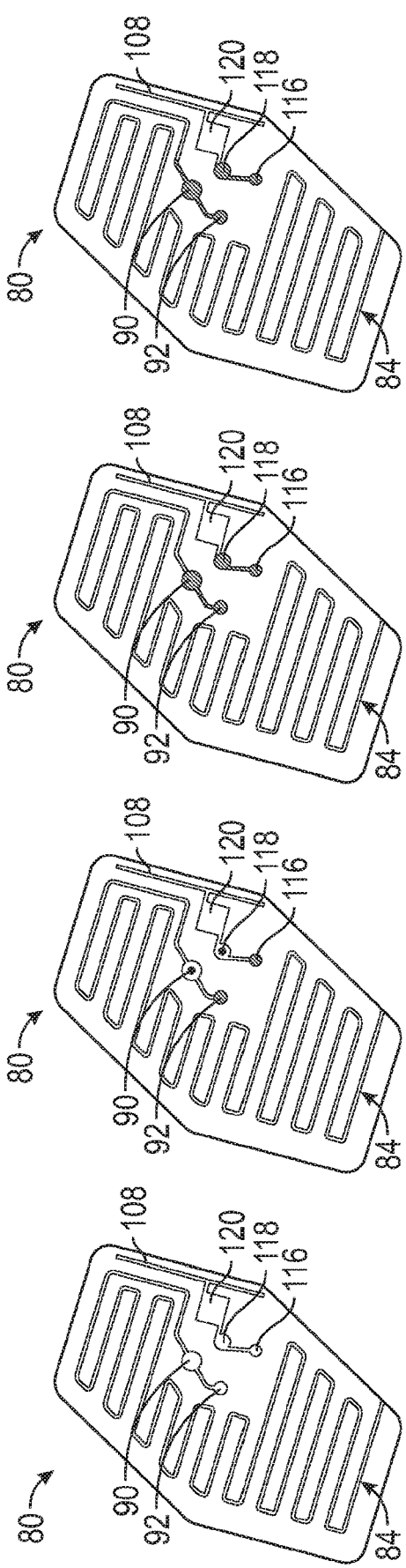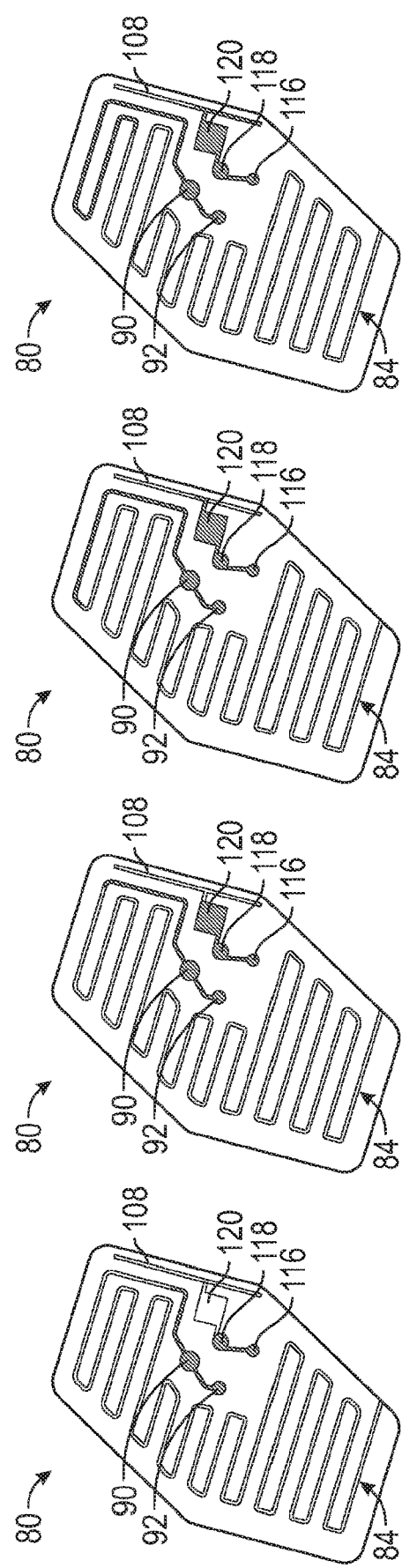

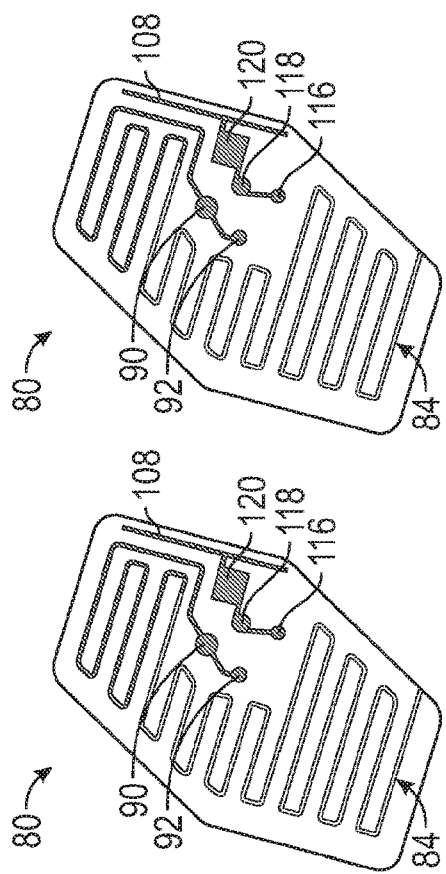
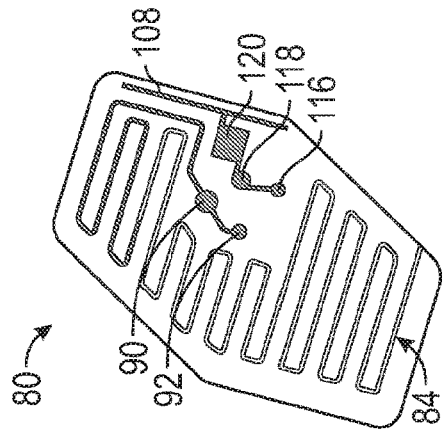
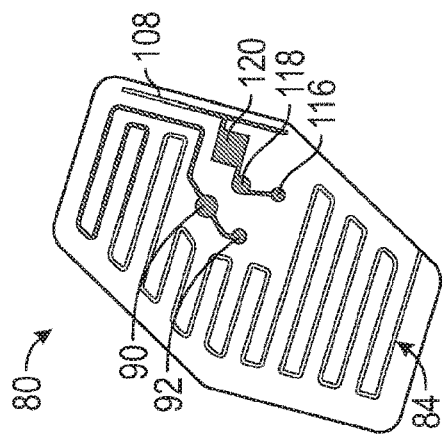
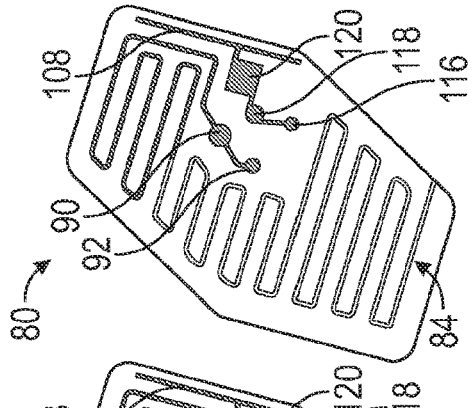
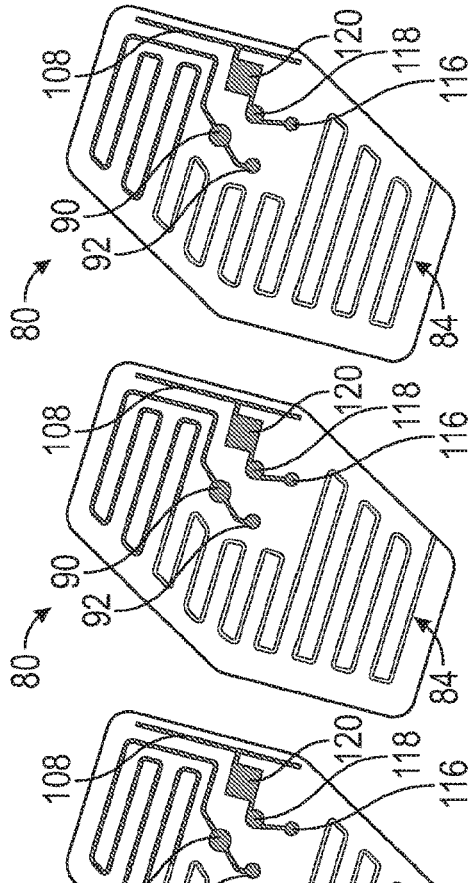
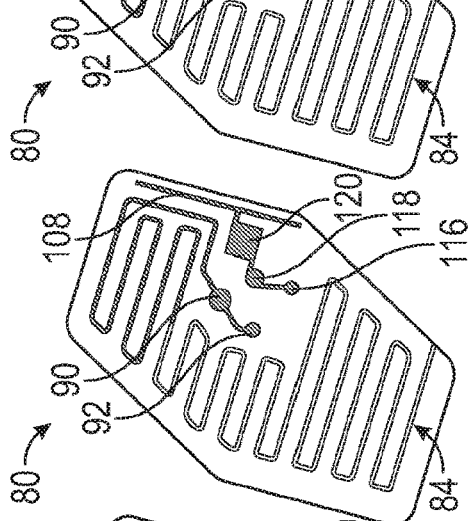
FIG. 21I FIG. 21J FIG. 21K FIG. 21L
FIG. 21M FIG. 21N FIG. 21O FIG. 21P FIG. 21Q

WEARABLE FLUIDIC DEVICE AND SYSTEM FOR SWEAT COLLECTION AND EXTRACTION

BACKGROUND OF THE INVENTION

This invention relates in general to wearable fluidic systems for collecting, measuring, and/or monitoring sweat rate, sweat loss, sweat volume, sweat composition, and/or biochemical information about one or more persons. In particular, this invention relates to an improved, wearable sweat collection device that captures or collects a known volume of skin bio-fluid, such as sweat, that may be later extracted from the sweat collection device and analyzed, and a method for collecting sweat using the improved, wearable sweat collection device.

The fields of sport physiology, health diagnostics, and forensic toxicology rely on the detection of biomarkers, xenobiotics, alcohol, and biological exposures through the analysis of blood, urine, saliva, skin excretions, and sweat. Although blood and urine are the most commonly used biological targets, there is growing interest in the use of non-invasive bio-fluids such as sweat and saliva because they are more readily accessible than other bodily fluids.

Recent research studies have established that xenobiotics and important biomarkers, for example chloride for cystic fibrosis diagnostics, are secreted in sweat. However, there are important analytical and quality challenges associated with known collection and extraction techniques, which limit the utility of such techniques in forensic toxicology and in health diagnostics. Currently, several groups and commercial organizations have developed occlusive wearable patches that use absorbent pads as a means to trap sweat solute and water as sweat leaves the skin pores. These patches may absorb within the range of about 100 µL to about 1200 µL of sweat, but the volume of sweat collected, and an instantaneous rate of sweat loss, cannot be easily measured using these pad-based devices. Occlusive patches may also cause skin irritation and may alter the microenvironment of the skin due to bacterial growth and poor aeration.

Developments that are more recent employ non-occlusive patches with transparent air permeable films that allow oxygen, carbon dioxide, and water vapor to escape while trapping sweat solutes and traces of drugs. These breathable patches reduce skin irritation and may be worn for several days with high compliance. As used herein, the term "compliance" refers to user compliance, i.e., how closely and how often a user or wearer follows the guidelines for use of a device. With a sweat collection device that is uncomfortable to wear or difficult to use, the wearer is significantly less likely to use the device as directed. If the device is too uncomfortable to wear, the user simply may not wear the device as directed. If the device is difficult to apply to the skin, then the user may intend to follow the guidelines but may miss an essential step or two in the guidelines for application. Thus, both comfort and simplicity can each have significant impact on compliance.

Although breathable absorbent pads have been widely used and accepted in sports hydration studies, forensics, and for medical purposes, several important obstacles persist. For example, there is a lack of sweat volume and/or rate control, no visual read-out of sweat volume and/or rate is possible while the patch is on the body, captured fluid may escape thus preventing effective long-term storage, extraction procedures are susceptible to contamination, and the process requires trained professionals to properly execute.

Point-of-care wearable fluidic devices and/or systems have the potential to capture known amounts of sweat, measure sweat rates, and facilitate extraction of captured sweat into laboratory vials for rapid diagnostics testing using benchtop analysis. Several forms of wearable, electronic, interstitial fluid, and sweat analysis systems exploit electrochemical approaches for monitoring biomarker concentrations, but do not allow for collection, capture, or subsequent analysis of discrete samples of sweat at well-defined time points. Known methods rely on gauze filter paper, or absorbent patches, such as for example a PharmChek® sweat patch, or coiled tubes, such as the Macroduct® sweat collection system, and serve only as passive vehicles for collecting sweat for post-hoc analysis. These conventional devices are expensive, bulky, heavy, unattractive aesthetically, and mechanically rigid. Thus, the conventional devices prevent intimate coupling with skin, especially soft, fragile skin, during physical exercise or intensive activity, exhibit poor signal quality, and physically disturb the user.

Thus, it would be desirable to provide an improved sweat collecting method and an improved wearable sweat collection device that overcomes the limitations of conventional wearable devices and that is high quality, low cost, is a component of an accessible health monitoring system, and that collects a known volume of sweat that may be later extracted from the sweat collection device and analyzed.

SUMMARY OF THE INVENTION

This invention relates to a wearable sweat monitoring system and a sweat sensing device for use therewith that allows a user to collect a known volume and rate of sweat that may be later extracted and analyzed.

A sweat collection device includes a flexible body having a first, outwardly facing surface and a second, skin-facing surface, and a sweat collection channel formed in the body, the sweat collection channel having a first end defining a sweat inlet port, and a second end defining a sweat outlet port. The sweat inlet port and the sweat outlet port are configured to be closed and sealed such that the sweat collection device and the collected sweat therein may be stored and shipped.

In another embodiment, a method of collecting sweat includes affixing a sweat collection device to the skin of a person, the sweat collection device including a flexible body having a first, outwardly facing surface and a second, skin-facing surface, and a sweat collection channel formed in the body, the sweat collection channel having a first end defining a sweat inlet port, and a second end defining a sweat outlet port. The sweat inlet port and the sweat outlet port are configured to be closed and sealed such that the sweat collection device and the collected sweat therein may be stored and shipped. The sweat inlet port is positioned on the skin of the person at a location from which sweat is desired to be collected and the sweat collection device is affixed to the skin. A first occlusion tab is affixed to the sweat inlet port and a second occlusion tab is affixed to the sweat outlet port after a desired volume of sweat has been collected in the sweat collection device. The first and second occlusion tabs define fluid-tight seals of the sweat inlet port and the sweat outlet port, respectively. The sweat collection device may then be removed.

In an additional embodiment, a sweat collection system includes a sweat collection device configured to be adhered to the skin of a user to collect sweat for storage, extraction, and analysis. The sweat collection device including a flexible body having a first, outwardly facing surface and a second, skin-facing surface, and a sweat collection channel formed in the body, the sweat collection channel having a first end defining a sweat inlet port, and a second end defining a sweat outlet port. A dye well formed in the sweat channel. A dye is disposed in the biochemical assay well and is positioned to react with sweat traveling through the sweat channel and to provide one of a visual indicator and an indicator detectable by a camera and connected processor of the flow of the sweat in the sweat channel. The sweat inlet port and the sweat outlet port are configured to be closed and sealed such that the sweat collection device and the collected sweat therein may be stored and shipped. The sweat inlet port is positioned on the skin of the person at a location from which sweat is desired to be collected and the sweat collection device is affixed to the skin. The sweat in the sweat collection channel is dyed with the dye in the dye well. A first occlusion tab is affixed to the sweat inlet port and a second occlusion tab is affixed to the sweat outlet port after a desired volume of sweat has been collected in the sweat collection device, the first and second occlusion tabs defining fluid-tight seals of the sweat inlet port and the sweat outlet port, respectively. A digital camera is connected to a processor and captures sequential images of an outwardly facing surface of the sweat collection device at predetermined time intervals while the sweat collection device is affixed to the skin to determine a total volume of sweat collected over a known period of time. A graph of sweat volume over time is then plotted to determine a sweat rate.

Various aspects of this invention will become apparent to those skilled in the art from the following detailed description of the preferred embodiment, when read in light of the accompanying drawings.

BRIEF DESCRIPTION OF THE DRAWINGS

FIG. 1 is a plan view of a first embodiment of a sweat collection device in accordance with this invention.

FIG. 2 is a plan view of a second embodiment of a sweat collection device in accordance with this invention.

FIG. 21A is a plan view of the sweat collection device illustrated in FIG. 1 showing the sweat collection device attached to a subject but prior to the subject beginning to sweat.

FIGS. 21B through 21Q are plan views of the sweat collection device illustrated in FIG. 21A showing the volume of sweat produced by the subject sequentially over time.

DETAILED DESCRIPTION OF THE PREFERRED EMBODIMENT

Figure 3:
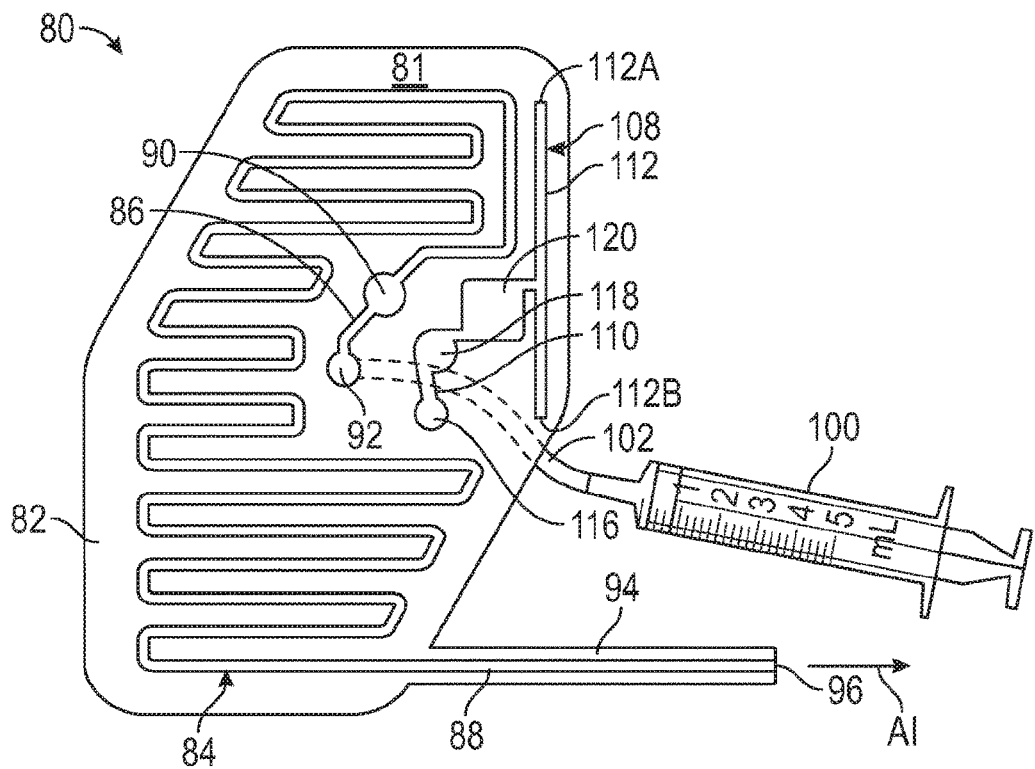
FIG. 3 is a plan view of the sweat collection device illustrated in FIG. 2 and showing a first embodiment of a method of extracting a collected sample of skin bio-fluid from the sweat collection device.

The present invention is directed to a wearable sweat collection device that collects a known volume of skin bio-fluid, such as sweat, from persons, such as athletes, military personnel, patients, including remote patients (e.g. hyperhidrosis patients) and drug rehabilitation patients, and newborns. The collected sweat may be later extracted from the sweat collection device and analyzed. The invention is further directed to a method of collecting, storing, analyzing, and extracting sweat for sports, forensic toxicology, health diagnostics, hyperhidrosis, and neonatal care.

The wearable sweat collection device is a skin-mounted device that contains inlet and outlet ports. Sweat from skin pores enters into the sweat collection device and perfuses through sweat microchannels therein until the sweat reaches the outlet port. The material covering the microchannels is transparent, providing optical access to the progression of sweat in the microchannels over time. Using this sweat collection device, an operator can determine a total sweat volume collected over a predetermined time. Based on a simple visual inspection, coaches, physicians, patients, toxicologists, or others can monitor the total sweat volume collected and a sweat volume rate, and use this and additional information to decide when to remove the wearable sweat collection device from the skin and extract the collected sweat sample into a container for further analysis.

The collected sweat sample may, for example, be stored for analysis of endogenous and exogenous chemicals in the sweat. The sweat samples that are collected and then extracted from the wearable sweat collection device may also indicate a sweat rate and total local sweat loss. The wearable sweat collection device further includes an outlet port that is configured to facilitate transfer of the collected sweat into conventional fluid collection vials or containers for rapid analysis and the identification of sweat biomarkers and exogenous chemicals. For example, the collected sweat that has been extracted from the wearable sweat collection device may be tested for biomarkers including but not limited to chloride, sodium, zinc, magnesium, pH, potassium, calcium, proteins, micro-RNA, DNA, xenobiotics including but not limited to cocaine metabolites, opiates, cannabis, and amphetamines, and alcohol including but not limited to ethanol.

The wearable sweat collection device inlet and outlet ports may also be temporarily sealed, enabling long-term storage of sweat samples for extraction at a later time.

The improved sweat collection device and improved method of collecting, storing, analyzing, and extracting sweat facilitate collecting and extracting sweat efficiently with minimal loss during transfer, and minimizes undesirable interaction of the collected sweat with foreign substances. Additionally, the sweat collection device preserves the sweat in its original liquid form, thus maintaining validity in measuring sweat composition, and ensuring ease of analysis and ease of transfer.

As described in detail below, the sweat monitoring system may relay information to the subject or other interested party in real time by analyzing images of fluid or sweat microchannels within the sweat collection device with a camera, such as a smartphone camera.

Referring now to the drawings, there is illustrated in FIGS. 1 through 6 a first embodiment of a sweat collection device 80 in accordance with this invention and described in detail below.

Referring again to the drawings, there are illustrated in FIGS. 7 through 17 examples of embodiments of a sweat sensing device 10 and 50. The illustrated sweat sensing devices 10 and 50 are conventional in the art, have been described and illustrated in PCT Application No. PCT/US18/43430, and are intended to illustrate one way that the improved sweat collection device 80 according to this invention may be constructed.

The sweat sensing device 10 includes a substantially flexible body 11 having a first or upper layer 12, a second layer 14, a third layer 16, a fourth layer 18, and a fifth or lower layer 20. The upper layer 12 has a first or outwardly facing surface 22. The lower layer 20 has a second or skin-facing surface 24. An adhesive is applied to the skin-facing surface 24, and the skin-facing surface 24 is covered by a removable adhesive liner 25 formed from any desired flexible and air/oxygen impermeable material.

The illustrated first layer 12 and the illustrated fifth layer 20 are formed from clear polyurethane having a thickness of about 0.004 inches (0.10 mm) Alternatively, the first layer 12 and the fifth layer 20 may be formed from other desired soft, flexible, and clear material, such as silicone, polyethylene, polyethylene terephthalate (PET), or polyurethane. If desired, the fifth layer 20 may be formed from an opaque material. The first layer 12 and the fifth layer 20 may also have other desired thicknesses. For example, the first layer 12 may have a thickness within about 0.002 in to about 0.006 in (about 0.05 mm to about 0.15 mm), and the fifth layer 20 may have a thickness within about 0.001 in to about 0.004 in (about 0.025 mm to about 0.10 mm).

The illustrated third layer 16 is formed from clear silicone having a thickness of about 0.005 inches (0.127 mm) Alternatively, the third layer 16 may be formed from other desired soft, flexible, and clear material, such as polyurethane, polyester, or PET, and may have other desired thicknesses, such as within about 0.004 in to about 0.006 in (about 0.10 mm to about 0.15 mm).

The illustrated second layer 14 and the illustrated fourth layer 18 are formed from clear acrylic PSA having a thickness of about 0.002 inches (0.50 mm) The second and fourth layers 14 and 18 are adhesive layers that bond the first layer 12, the third layer 16, and the fifth layer 20 together. The material chosen for the adhesive second and fourth layers 14 and 16 may vary based on the material of the layers to which they are applied. For example, a silicon adhesive layer may be chosen to a bond silicon layers together. Alternatively, the second and fourth layers 14 and 18 may have other desired thicknesses, such as within about 0.001 in to about 0.004 in (about 0.025 mm to about 0.10 mm) If desired, the first layer 12, the third layer 16, and the fifth layer 20 may be directly bonded together by any conventional means, such as by ultrasonic welding.

One or more sweat channels may be formed in at least the third layer 16. As shown in embodiment of the sweat sensing device 10 illustrated in FIGS. 9 through 13, a first sweat channel 26 is formed in the third layer 16 and defines a serpentine pathway. Alternately, and as shown in the illustrated embodiment of the sweat sensing device 10, the first sweat channel 26 is also formed in the second and fourth layers 14 and 18, respectively. The first sweat channel 26 has a sweat inlet end 28 and a sweat outlet end 30 at a peripheral edge of the sweat sensing device 10 and positioned to allow sweat to exit the first sweat channel 26. The first sweat channel 26 may also include a biochemical or assay well 32 near the sweat inlet end 28.

Additionally, a sweat channel may be formed such that portions of the sweat channel are variously formed in the second layer 14, the third layer 16, and in the fourth layer 18, or in combinations of layers, such as in the second and third layers 14 and 16 and in the third and fourth layers 16 and 18. Varying the height of the sweat channel throughout its length in this manner allows areas of greater sweat channel height to be positioned in the flexible body 11 as a visual indicator wherein a color change within the portions of the sweat channel having the greater height may be more easily seen because a larger volume of dye therein may appear darker in color.

When a sweat channel is formed having different heights throughout its length, i.e., when portions of the sweat channel are variously formed in the layers thereof, the sweat channel may crossover itself, allowing for a longer sweat channel without the need to increase the size of the sweat sensing device 10 and 50.

Figure 10:
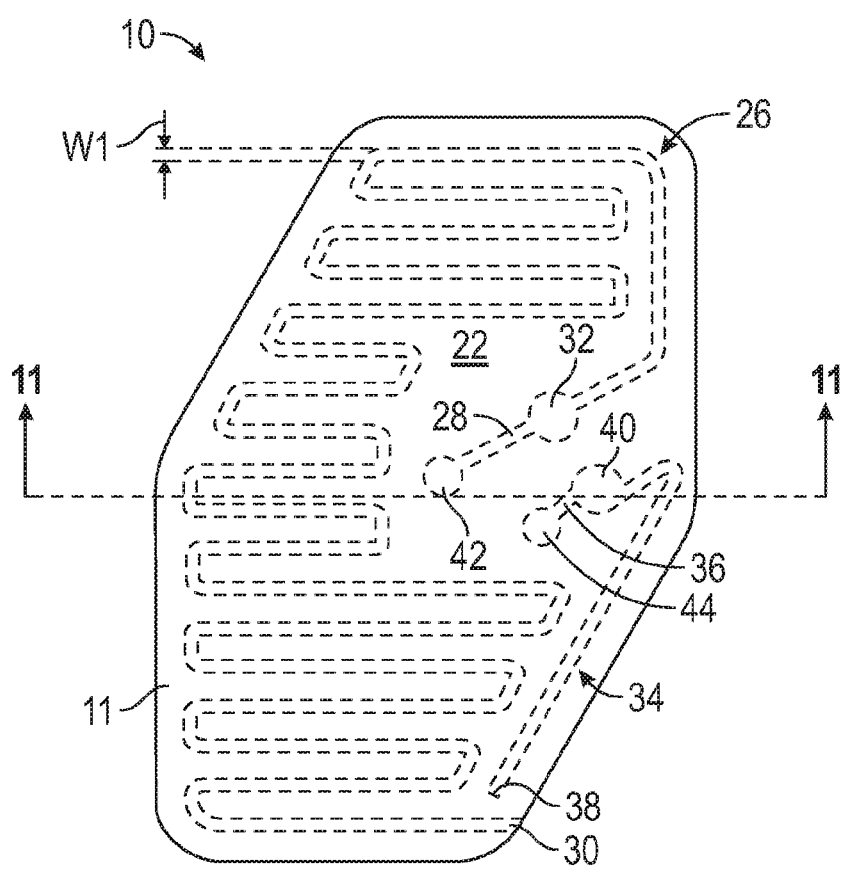
FIG. 10 is a plan view of a conventional sweat collection device.

As best shown in FIG. 10, a second sweat channel 34 is also formed in the second, third, and fourth layers 14, 16, and 18, respectively. The second sweat channel 34 has a sweat inlet end 36 and a second end 38 that, unlike the first sweat channel 26, does not define a sweat outlet. The second sweat channel 34 may also include a biochemical assay well 40 near the sweat inlet end 36.

The lower layer 20 may have fluid or sweat inlet ports in fluid communication with the sweat channels. As best shown in FIG. 10, the lower layer 20 includes a first sweat inlet port 42 in fluid communication with the first sweat channel 26, and a second sweat inlet port 44 in fluid communication with the second sweat channel 34. In the illustrated embodiment of the sweat sensing device 10, the biochemical assay wells 32 and 40 extend through the lower layer 20 to allow for the insertion a chemical assay therein.

Figure 11:
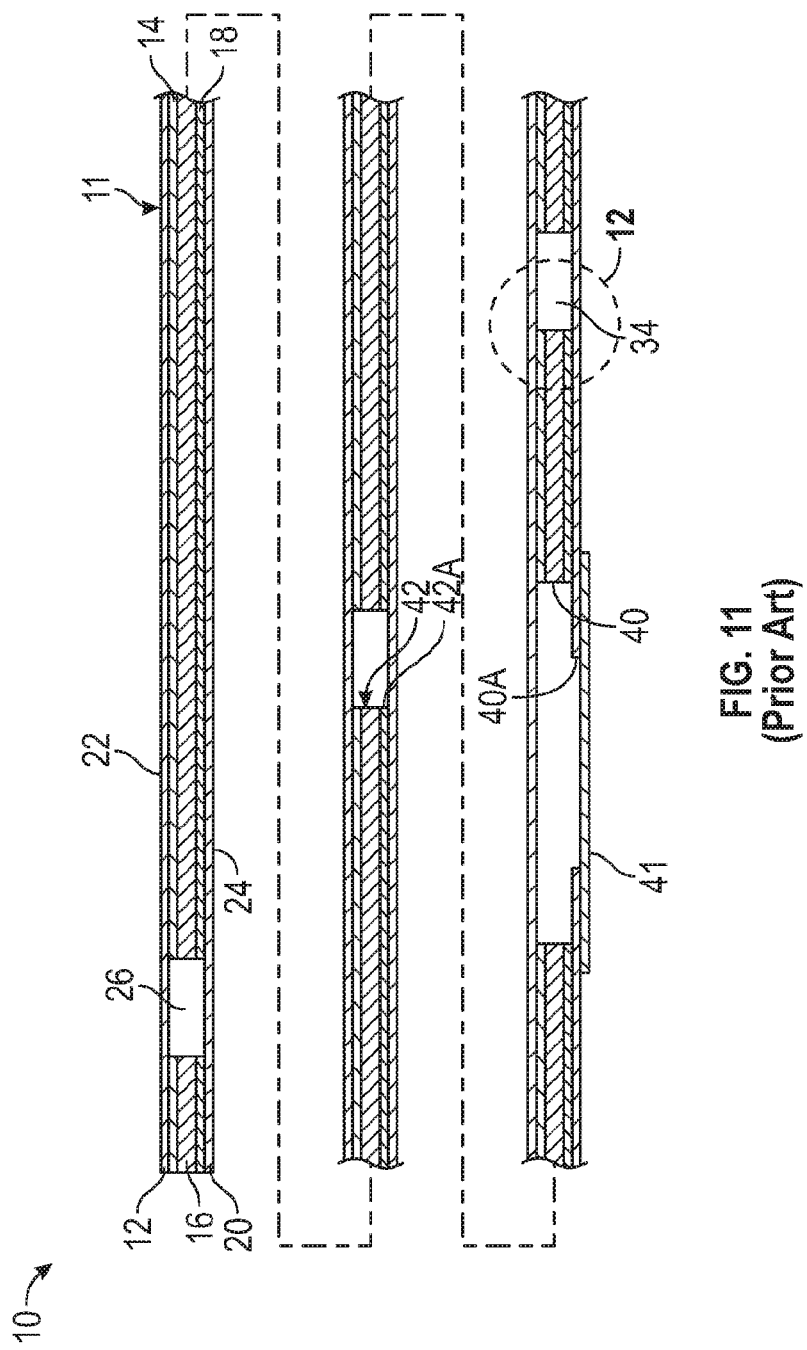
FIG. 11 is a cross-sectional view taken along the line 11-11 of FIG. 10.

As shown in FIG. 11, a portion 42A of the first sweat inlet port 42 in the lower layer 20 may be smaller than the portions of the first sweat inlet port 42 formed in the second, third, and fourth layers, 14, 16, and 18, respectively. Similarly, a portion 40A of the biochemical assay well 40, and a portion (not shown) of the biochemical assay well 32, in the lower layer 20 may be smaller than the portions of the biochemical assay wells 40 and 32 formed in the second, third, and fourth layers, 14, 16, and 18, respectively.

After the assay wells 32 and 40 are formed and the sweat sensing devices 10 and 50 are assembled, a desired biochemical or chemical assay material, described in detail below, may be disposed therein. The assay wells 32 and 40 may then be closed with an adhesive layer 41, formed from any desired flexible material, such as the same material as the lower layer 20 to which the adhesive layer 41 is attached.

Figure 14:
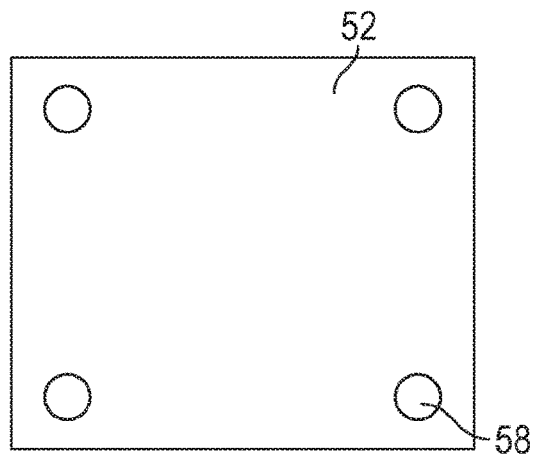
FIG. 14 is a plan view of a blank of material of an upper layer of an alternate embodiment of the sweat collection device illustrated in FIG. 10.
Figure 15:
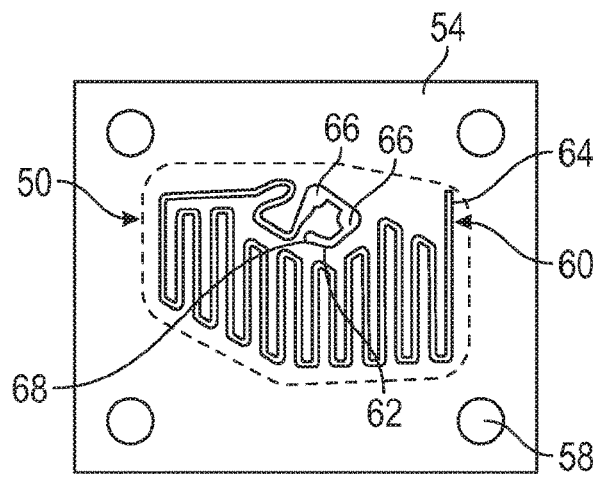
FIG. 15 is a plan view of a blank of material of one of an inner layer of the sweat collection device illustrated in FIG. 14.
Figure 16:
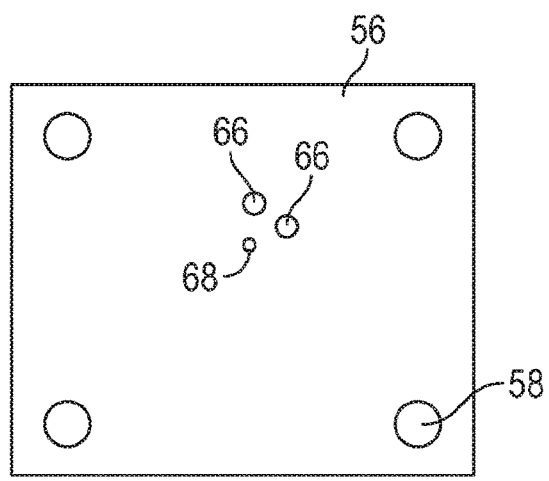
FIG. 16 is a plan view of a blank of material of a lower layer of the sweat collection device illustrated in FIGS. 14 and 15.
Figure 17:
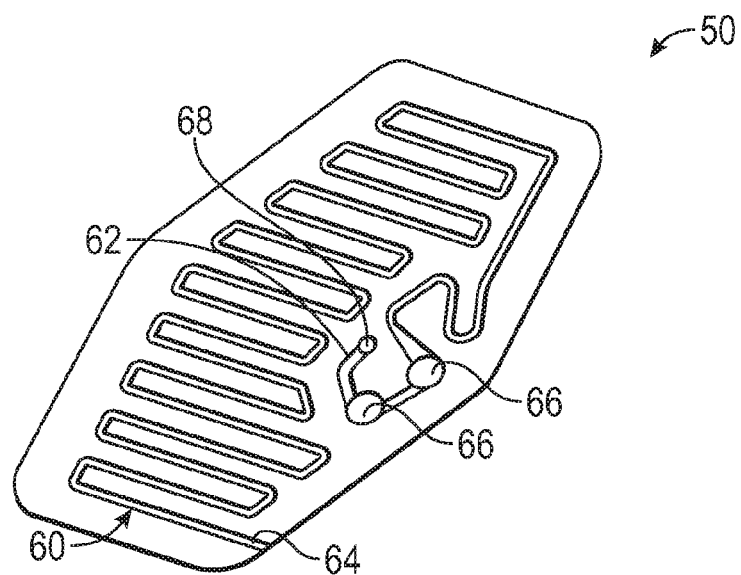
FIG. 17 is a plan view of the sweat sensing device formed from the layers illustrated in FIGS. 14 through 16.

The sweat channels and ports may be formed in the second, third, fourth, and fifth layers 14, 16, 18, and 20 by any desired means, such as with a laser, or die cut. For example, sheets or blanks of material comprising the layers of a second embodiment of a sweat sensing device 50 are shown in FIGS. 14 through 16. The assembled sweat sensing device 50 is also shown in FIG. 17. For example, FIG. 14 is a plan view of a sheet or blank of material of a first or upper layer 52 of the sweat sensing device 50. FIG. 15 is a plan view of a blank of material of one of an inner layer 54 of the sweat sensing device 50, such as any one of the second, third, fourth layers 14, 16, and 18 of the sweat sensing device 10 described above. FIG. 16 is a plan view of a blank of material of a lower layer 56 of the sweat sensing device 50. Each of the blanks 52, 54, and 56 include alignment holes 58 formed therein for aligning the blanks 52, 54, and 56 in a fixture, jig, or similar device (not shown).

As shown in FIG. 15, the inner layer 54 has a first sweat channel 60 formed therein. The first sweat channel 58 has a sweat inlet end 62 and a second end 64. The first sweat channel 58 may also include one or more biochemical assay wells 66 near the sweat inlet end 60.

The lower layer 56 may have a sweat inlet port in fluid communication with the sweat channel. As best shown in FIG. 16, the lower layer 56 includes a first sweat inlet port 68 in fluid communication with the first sweat channel 58. The one or more biochemical assay wells 66 extend through the lower layer 56.

It will be understood that a width W1 of the sweat channels, and a diameter of the assay wells, in the embodiments of the improved sweat sensing devices described herein may vary with the specific application of the sweat sensing device. The illustrated sweat channels 26, 34, and 60 may have any desired width W1, such as width of about 0.040 in (1.0 mm) Alternatively, the sweat channels 26, 34, and 60 may have a width W1 within about 0.005 in to about 0.120 in (about 0.127 mm to about 0.30 mm) The inlet ports 42, 42, and 68 and the biochemical assay wells 32, 40, and 66 may have any desired diameter, such as diameter of about 0.040 in and 0.160 in (about 1.00 mm and 4.00 mm), respectively. Alternatively, the inlet ports 42, 42, and 68 may have a diameter of about 0.040 in to about 0.100 in (about 1.00 mm to about 2.50 mm), and the biochemical assay wells 32, 40, and 66 may have a diameter of about 0.020 in to about 0.200 in (about 0.50 mm to about 5.00 mm).

Although the illustrated inlet ports and assay wells are shown having a circular transverse section, the inlet ports and assay wells may be formed having other shapes, such as having a square transverse section, or other geometric shapes.

The biochemical assay wells 32 and 40 define colorimetric reaction sites that may be configured to react with very small, such as microliter volumes of sweat. The assay wells 32 and 40 may contain colored dyes, for example conventional food coloring dyes), chemical assays, fluoroscopic dyes, enzymatic assays, heavy metal assays, and protein/DNA based assays. In the sweat sensing device 10, one assay well 32 is formed in the sweat channel 26 and one assay well 40 is formed in the sweat channel 34. In the sweat sensing device 50, two assay wells 66 are formed in the sweat channel 60 near the sweat inlet port 68.

It will be understood that the sweat sensing devices disclosed herein, such as the sweat sensing devices 10 and 50, may be formed such that the depths of the sweat channels and/or the assay well vary. The color change induced by a chemical reaction will vary with a depth of the sweat channel or assay well according to the Beer-Lambert law. Measuring the color change in the sweat sensing devices 10 and 50 at multiple depths may help reduce any negative effects related to lighting, exposure, and focus.

If desired, the outwardly facing surface 22 of the sweat sensing device 10 may be laminated with a very thin layer of polymer (not shown), such as a 25 μm layer of PET, having indicia printed thereon. The indicia may, for example, be aligned with the sweat channels 26 and/or 34 to highlight selected areas of the channels 26 and/or 34 for optical image capture.

Figure 9:
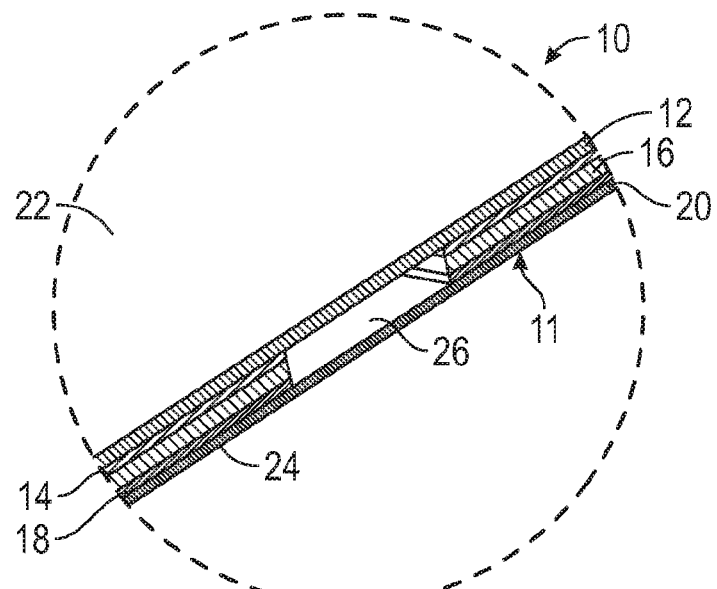
FIG. 9 is an enlarged cross-sectional view of the portion of the sweat collection device within circle 9 of FIG. 8.
Figure 12:
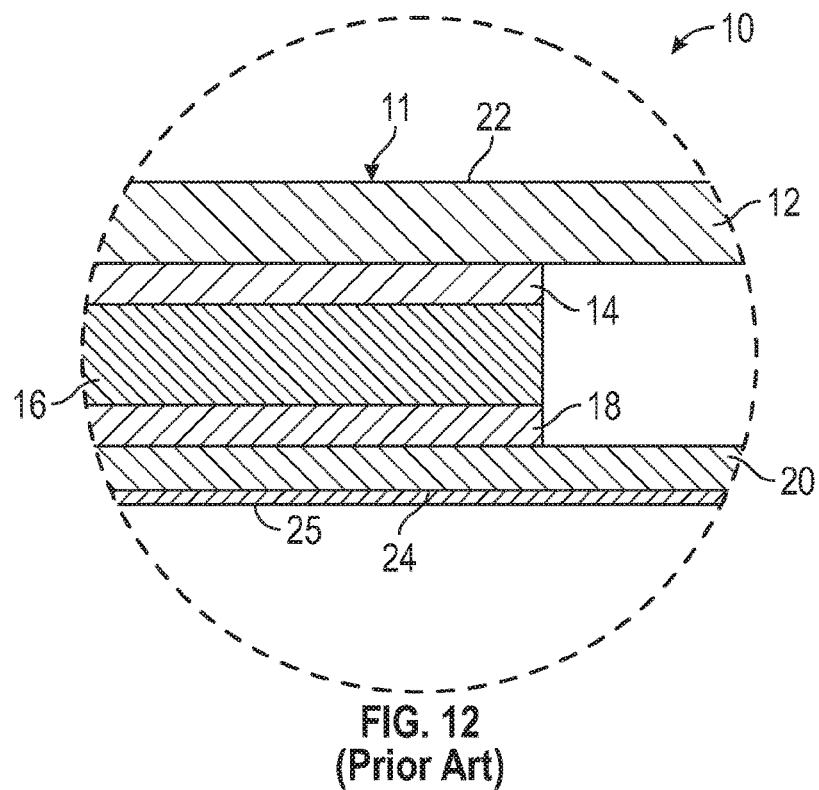
FIG. 12 is an enlarged cross-sectional view of the portion of the sweat collection device within circle 12 of FIG. 11.
Figure 13:
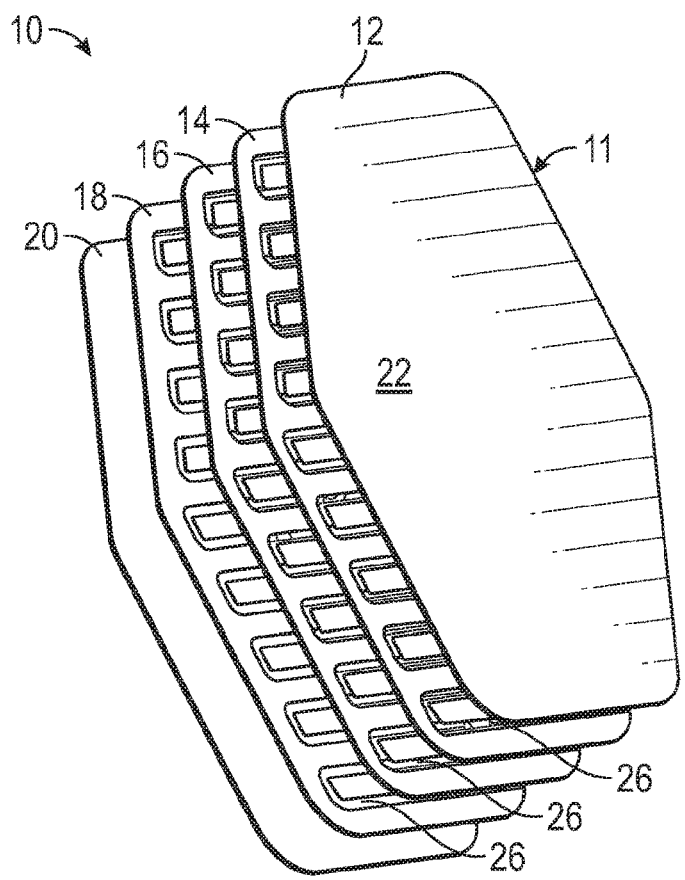
FIG. 13 is an exploded perspective view of the sweat collection device illustrated in FIGS. 10 through 12.

Referring again to FIGS. 1 through 6, the improved sweat collection device 80 includes a substantially flexible body 82 having a first outwardly facing surface 81, a second, skin-facing surface, and the plurality of the layers 12, 14, 16, 18, and 20 as shown in FIGS. 9, 11 and 12 and described above. For clarity, the skin-facing surface and the plurality of the layers 12, 14, 16, 18, and 20 are not shown in FIGS. 1 through 6. For example, the sweat collection device 80 may include the upper layer 12, the second layer 14, the third layer 16, the fourth layer 18, and the fifth or lower layer 20. As shown in FIGS. 9, 11, and 12, the upper layer 12 has an outwardly facing surface 22, and the lower layer 20 has a skin-facing surface 24. An adhesive may applied to the skin-facing surface 24, and the skin-facing surface 24 may be covered by a removable adhesive liner 25 formed from any desired flexible and air/oxygen impermeable material.

As in the embodiment of the sweat sensing device 10 illustrated in FIGS. 9, 11, and 12, the first layer 12 and the fifth layer 20 may be formed from clear polyurethane having a thickness of about 0.004 inches (0.10 mm) Alternatively, the first layer 12 and the fifth layer 20 may be formed from other desired soft, flexible, and clear material, such as silicone, polyethylene, polyethylene terephthalate (PET), or polyurethane. If desired, the fifth layer 20 may be formed from an opaque material. The first layer 12 and the fifth layer 20 may also have other desired thicknesses. For example, the first layer 12 may have a thickness within about 0.002 in to about 0.006 in (about 0.05 mm to about 0.15 mm), and the fifth layer 20 may have a thickness within about 0.001 in to about 0.004 in (about 0.025 mm to about 0.10 mm).

The illustrated third layer 16 is formed from clear silicone having a thickness of about 0.005 inches (0.127 mm) Alternatively, the third layer 16 may be formed from other desired soft, flexible, and clear material, such as polyurethane, polyester, or PET, and may have other desired thicknesses, such as within about 0.004 in to about 0.006 in (about 0.10 mm to about 0.15 mm).

The illustrated second layer 14 and the illustrated fourth layer 18 may be formed from clear acrylic PSA having a thickness of about 0.002 inches (0.50 mm) The second and fourth layers 14 and 18 are preferably adhesive layers that bond the first layer 12, the third layer 16, and the fifth layer 20 together. The material chosen for the adhesive second and fourth layers 14 and 16 may vary based on the material of the layers to which they are applied. For example, a silicon adhesive layer may be chosen to bond silicon layers together. Alternatively, the second and fourth layers 14 and 18 may have other desired thicknesses, such as within about 0.001 in to about 0.004 in (about 0.025 mm to about 0.10 mm) If desired, the first layer 12, the third layer 16, and the fifth layer 20 may be directly bonded together by any conventional means, such as by ultrasonic welding.

One or more microchannels or sweat channels may be formed in at least the third layer 16. As shown in FIGS. 1 through 6, a first sweat collection channel 84 is formed in the third layer 16 and defines a serpentine pathway. Alternately, and like the sweat channel 26 shown in the illustrated embodiment of the sweat sensing device 10, the first sweat collection channel 84 may also formed in the second and fourth layers 14 and 18, respectively.

Advantageously, the sweat collection device 80 is thus impermeant or mostly impermeant to gas, liquids, and water vapor. Preferably, the material of the layer or layers that define the first sweat collection channel 84 has a low moisture vapor transmission rate (MVTR) of less than about 600 g/m$^2$/24 hrs.

The first sweat collection channel 84 has a sweat inlet end 86 and a sweat outlet end 88 at a peripheral edge of the sweat collection device 80 that is positioned to allow sweat to exit the first sweat collection channel 84. The first sweat collection channel 84 may also include a biochemical assay or dye well 90 near the sweat inlet end 80.

The lower layer 20 of the sweat collection device 80 includes a first sweat inlet port 92 formed therein and in fluid communication with the first sweat collection channel 84. In the illustrated embodiment of the sweat collection device 80, the dye well 90 extends through the lower layer 20 to allow for the insertion a chemical assay or dye, described below in detail, therein.

The sweat inlet port 92 and the dye well 90 may have any desired diameter, such as diameter of about 0.040 in and 0.160 in (about 1.00 mm and 4.00 mm), respectively. Alternatively, the sweat inlet port 92, may have a diameter of about 0.040 in to about 0.100 in (about 1.00 mm to about 2.50 mm), and the dye well 90 may have a diameter of about 0.020 in to about 0.200 in (about 0.50 mm to about 5.00 mm).

In FIG. 1, the sweat outlet end 88 at a peripheral edge of the sweat collection device 80 also defines a sweat outlet port. Preferably, the flexible body 82 of sweat collection device 80 is formed with a longitudinally extending flexible fluidics tail or outlet member 94 that defines a sweat outlet port 96. As shown in FIGS. 2 through 6, the outlet member 94 extends outwardly from a peripheral edge of the flexible body 82 and the first sweat collection channel 84 extends through the outlet member 92 to the sweat outlet port 96.

Figure 5:
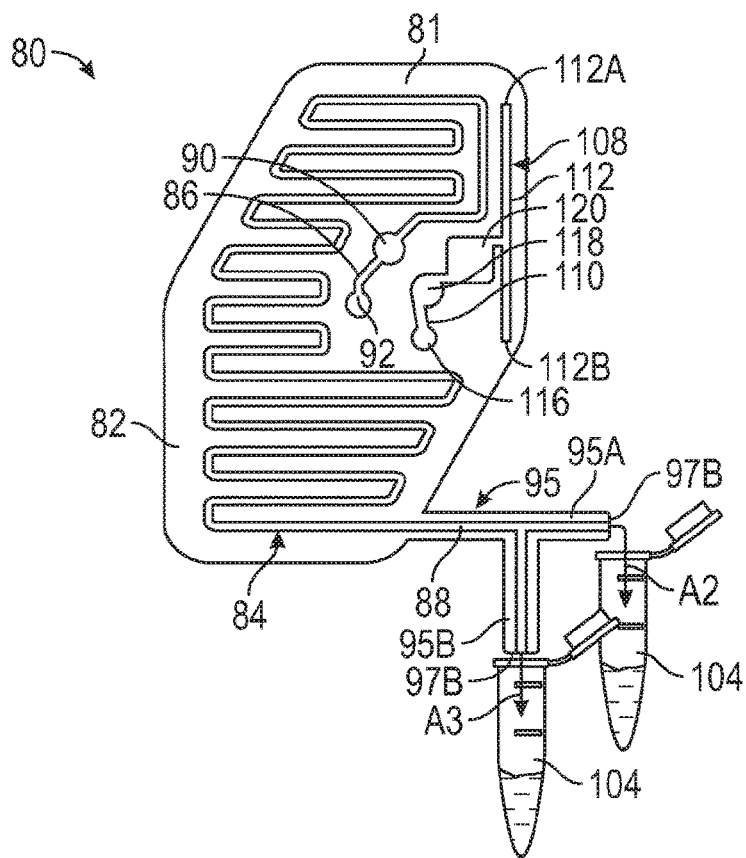
FIG. 5 is a plan view of the sweat collection device illustrated in FIGS. 2 through 4 having an alternate embodiment of an outlet member and showing the collected sample of skin bio-fluid being simultaneously collected into two storage containers.

The sweat collection device 80 may be formed with an alternative embodiment of the outlet member 95. As shown in FIG. 5, the outlet member 95 includes a longitudinally extending first portion 95A that is substantially similar to the outlet member 94 and a longitudinally extending second portion 95B that is in fluid communication with the first portion 95A and extends transversely therefrom. The first portion 95A defines a sweat outlet port 97A and the second portion 95B defines a sweat outlet port 97B. If desired, the distal ends of the outlet member 94, the first portion 95A, and the second portion 95B may be tapered to facilitate the extraction of fluid.

The dye well 90 defines a colorimetric reaction site that may be configured to react with very small, such as micro- liter volumes of sweat. The dye well 90 may contain a colored dye, for example a conventional food color dye, such as Americolor Soft Gel Paste 102, and may be deposited in the dye well 90 with a micropipette, a syringe, or a small needle. Alternatively, a chemical assay, a fluoroscopic dye, an enzymatic assay, a heavy metal assay, and a protein/DNA based assay may be used. Preferably, the dye is an uncharged and non-reactive dye that contains none of the chemicals that the user is interested in detecting. For example, if the sweat will be tested for chloride, then a dye containing no chloride will be use.

In other embodiments, the dye may be chosen to be free of sodium, potassium, glucose, lactate, and other substances of interest to enable tests for those chemicals. The colored dye advantageously provides a real time visual indication of the volume of sweat collected in the sweat collection device 80. The dye may also be used to help track an instantaneous sweat rate by noting the position of the dye in the first sweat collection channel 84 over time. The dye also eases extraction of sweat from the sweat collection device 80 because the operator can more clearly see when the dyed sweat has been fully extracted from the first sweat collection channel 84.

To use the sweat collection device 80, the removable adhesive liner 25 is removed from the skin-facing surface 24, and the skin-facing surface 24 is affixed to the skin of the person being monitored. The sweat collection device 80 may be adhered anywhere on the person being monitored, including but not limited to the forearm, head, shoulders, arms, hands, torso, chest, legs and feet. Additionally, the sweat collection device 80 may collect within the range of about 5 μL to about 500 μL of sweat from the person being monitored during, after, or both during and after completion of an exercise or physical exertion routine or through electrochemical sweat induction by application of, for example, pilocarpine and electrical stimulation.

Once affixed to the skin of the person being monitored, sweat from the person being monitored enters the first sweat collection channel 84 of the sweat collection device 80 through the first sweat inlet port 92. Upon reaching the dye well 90, the sweat reacts with the dye in the dye well 90, changes color, such as to orange, and therefore becomes visible to the unaided eye.

Although the sweat collection device 80 is illustrated having the dye well 90 formed therein, it will be understood that the sweat collection device 80 may be formed without the dye well 90, for example in embodiments wherein a dye is not required or not desired. Alternatively, in embodiments wherein a dye is not required or not desired, the sweat collection device 80 may be formed having the dye well 90 formed therein, but without having a dye provided therein.

Figure 19A:
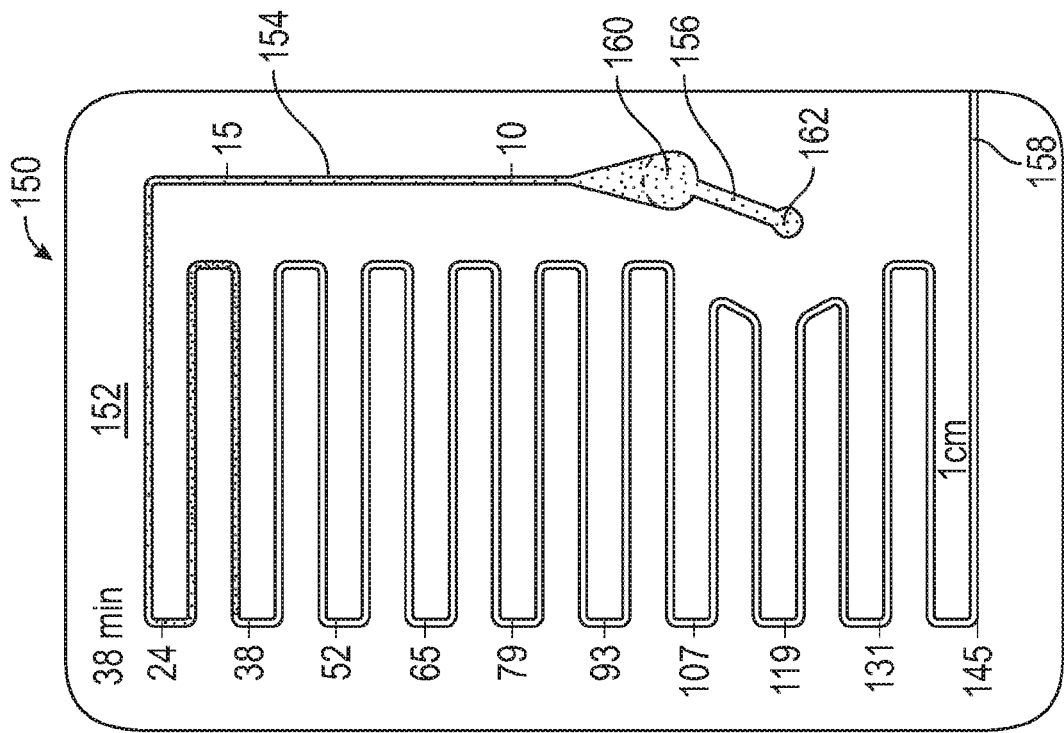
FIG. 19A a plan view of a fourth embodiment of a sweat collection device in accordance with this invention showing an upper surface thereof having numeric volume markings.
Figure 19B:
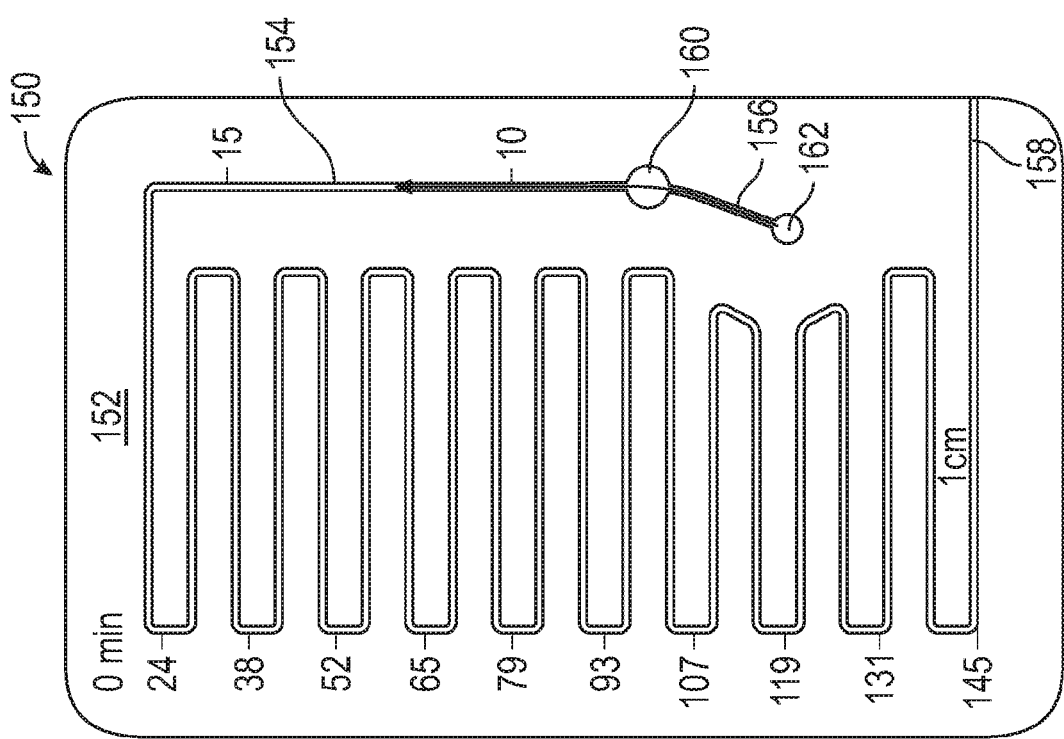
FIG. 19B a plan view of sweat collection device illustrated in FIG. 19A showing the flow of skin bio-fluid at 38 minutes.

Referring to FIGS. 19A and 19B, an outwardly facing surface 152 of a fourth embodiment of a sweat collection device 150 is shown. The illustrated sweat collection device 150 has a sweat channel 154 formed therein. The sweat channel 154 has a sweat inlet end 156 and a sweat outlet end 158 at a peripheral edge of the sweat collection device 150 and positioned to allow sweat to exit the first sweat channel 154. The first sweat channel 154 may also include a biochemical assay or dye well 160 near the sweat inlet end 156.

The lower layer (not shown) of the sweat collection device 150 includes a sweat inlet port 162 formed therein and in fluid communication with the sweat channel 154.

As shown in FIGS. 19A and 19B, the outwardly facing surface of the sweat collection device 150, i.e., the visible surface of the sweat collection device 150, may include visual landmarks indicating a volume of fluid that corresponds to the visible fluid progression through the sweat channel 154. Once the leading edge of the visible sweat passes a desired target region in the sweat channel 154, the operator may note the volume, or may capture an image of the sweat collection device 150, such as with the camera of a smartphone (not shown). The sweat collection device 150 may then be removed.

The image of the sweat volume in the first sweat collection channel 84, 154 may be analyzed in real time by an algorithm in an application within the smartphone. Alternatively, an image of the sweat collection device 80, 150 may be captured by a digital camera (not shown), transferred to a processor, such as in a computer (not shown), and analyzed by an algorithm in the computer (not shown).

Alternatively, a sweat rate may be instantaneously or nearly instantaneously obtained by noting the volume of sweat collected inside a sweat channel, such as the sweat channel 154, and further noting the elapsed time. Alternatively, a smartphone (not shown) may be used to successively image and timestamp sweat volume and the progression of sweat through the sweat channel 154. For example, an operator can: (1) use the smartphone (not shown) to capture an image of the sweat in the sweat channel 154 with an associated timestamp, (2) calculate a volume of sweat from the image or images using image processing software and display the instantaneous sweat rate, and (3) compute the volume of sweat from the image or images over several time periods and graph the sweat rate over each period of time.

The instantaneous sweat rate tracked with a smartphone through the course of an exercise regimen can show real time differences in sweat rate during all or a portion of the exercise regimen. This data, alone or in combination with temperature data captured, such as by the temperature sensing channel 140 described herein, can indicate different levels of a user's effort and exertion or a period of transition from one activity to another. This information may be used to inform the user, physician, a coach, or a training staff in athletic environments, whether alterations to the activity need to occur, for example, reducing exertion to stay within a certain training zone, increasing exertion to increase aerobic benefit from the activity, and/or predicting the onset of dehydration when the sweat rate becomes too high.

It will be understood that the visual landmarks indicating a volume of fluid that corresponds to the visible fluid progression through the sweat channel 154 shown on the outwardly facing surface of the sweat collection device 150 in FIGS. 19A and 19B may also be provided on the embodiments of the sweat collection devices 80 illustrated in FIGS. 1 through 6.

FIG. 21A is a plan view of the sweat collection device 80 illustrated in FIG. 1 showing the sweat collection device 80 as it would appear attached to a subject but prior to the subject beginning to sweat. FIGS. 21B through 21Q are plan views of the same sweat collection device 80 illustrated in FIG. 21A showing the volume of sweat produced by the subject sequentially over time.

Thus, the sweat collection device 80 can capture instantaneous sweat rates by using a smartphone camera to capture images of the sweat collection device 80 while it is worn on the body. FIG. 21A, for example, illustrates the sweat collection device 80 when first affixed to a person, such as to the person's forearm. FIGS. 21B through 21L show a progression of the sweat through the first sweat collection channel 84 at intervals of about 5 minutes. FIGS. 21M through 21Q show a progression of the sweat through the first sweat collection channel 84 at intervals of about 2 minutes. FIG. 21K marks the end of a period of exercise and FIGS. 21L through 21 Q represent a cool-down period. Thus, each of FIGS. 21A through 21Q corresponds to total volume of sweat collected over a known period of time. With this data, sweat volume over time may be plotted on a graph to determine a sweat rate.

Advantageously, the sweat collection device 80 can capture instantaneous sweat rates as a wearer performs different activities. Sweat volume over time may be plotted separately for each activity to determine the sweat rate associated with that activity. The sweat rate for each activity may then be used to derive metrics related to each activity, for example, a relative level of exertion.

If desired, the first sweat inlet port 92 and the sweat outlet port 96 may closed and sealed after a desired volume of sweat has been collected. Once the first sweat inlet port 92 and the sweat outlet port 96 are sealed, the sweat collection device 80 may be stored, temporarily or long term, such as in a refrigerated container (not shown), and later shipped to a location where the sweat may be extracted and analyzed, such as a laboratory. As best shown in FIG. 2, the first sweat inlet port 92 and the sweat outlet port 96 may be sealed with occlusion tabs 98. The occlusion tabs 98 are preferably adhesive backed and may be relatively small, but large enough to close and seal each of the first sweat inlet port 92 and the sweat outlet port 96. The illustrated occlusion tabs 98 are circular, but it will understood that the occlusion tabs 98 may have any desired shape and size configured to close and seal the first sweat inlet port 92 and the sweat outlet port 96. The occlusion tabs 98 are preferably formed a material similar to the material of the third layer 16, such as silicone or other desired soft, flexible, and material, including but not limited to polyurethane, polyester, and PET. Preferably, the material of the occlusion tabs 98 also have an MVTR of less than about 600 $g/m^2/24$ hrs.

If desired, the pH sensor (not shown) and/or the temperature sensing channel 140, described below, may be provided on the sweat collection device 80 and may therefore provide information about the state of the collected sweat sample while the sweat collection device 80 is kept in storage.

Figure 4:
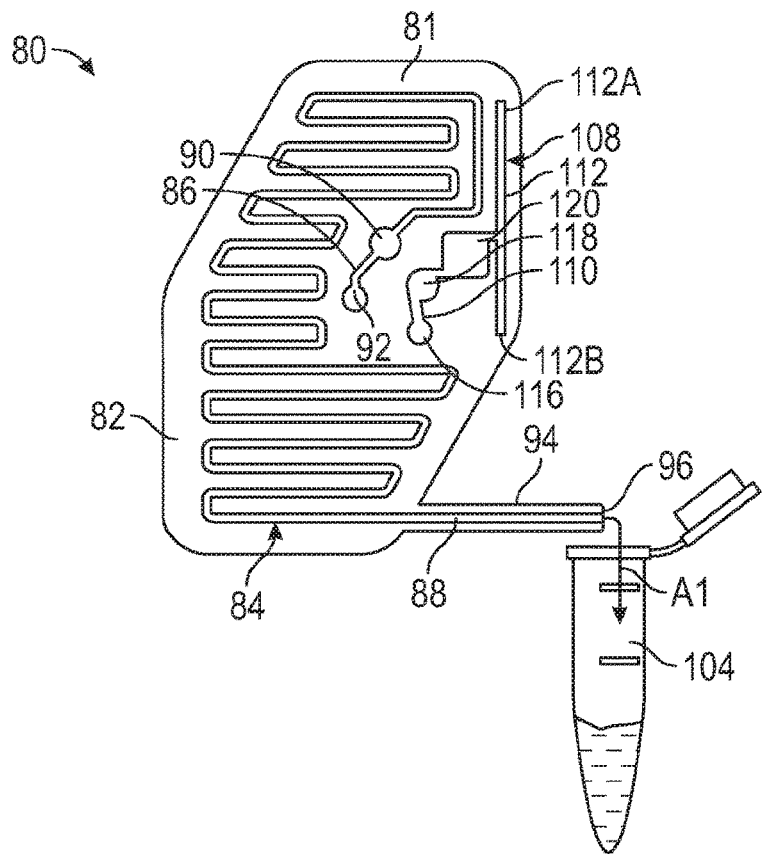
FIG. 4 is a plan view of the sweat collection device illustrated in FIGS. 2 and 3 showing the collected sample of skin bio-fluid being collected into a storage container.

Referring now to FIGS. 3 through 5, a first method of extracting sweat from the sweat collection device 80 is shown. As shown, a syringe 100 has a tube 102 attached thereto. The tube 102 may be any desired tube, such as a Tygon® tube. A distal end of the tube 102 has a size corresponding to the size of the first sweat inlet port 92, such as about 0.040 in (1.0 mm) The tube 102 may then be coupled to the first sweat inlet port 92 and define an airtight seal. The operator may next inject air stored in the syringe 100 through the tube 102 and into the first sweat collection channel 84. As air is pushed through the first sweat collection channel 84, the collected sweat is caused to move toward and through the sweat outlet port 96 (see the arrow A1).

The sweat outlet port 96 of the outlet member 94 may be positioned in or near the opening of a conventional fluid collection vial or container 104, such that the collected sweat is directed from the sweat outlet port 96 into the collection container 104 (see the arrow A1). Upon extraction of all the collected sweat in the sweat collection device 80, the collection container 104 may be sealed for storage and subsequent processing and analysis. Advantageously, this method allows for the extraction of most or all of the sweat collected in the sweat collection device 80 into the collection container 104 with minimal loss.

It will be understood that the air pushed from the syringe 100 produces a pressure front that exerts a force on the sweat in the first sweat collection channel 84. This force is larger than a force exerted by the atmosphere at the sweat outlet port 96, i.e., a force greater than 0 Atm gauge pressure, creating a pressure gradient from the first sweat inlet port 92 to the sweat outlet port 96, and forcing the sweat to move through the first sweat collection channel 84 and the outlet member 94 to the external collection container 104.

Referring to FIG. 5, the sweat collection device 80 is shown with the alternative embodiment of the outlet member 95. The method of extracting sweat from the sweat collection device 80 through the outlet member 95 is similar to the method of extracting sweat through the outlet member 94. As shown in FIG. 5, the sweat outlet port 97A of the first portion 95A may be positioned in or near the opening of a first conventional fluid collection container 104, such that the collected sweat is directed from the sweat outlet port 97A into one of two conventional fluid collection containers 104 (see the arrow A2). At the same time, the sweat outlet port 97B of the second portion 95B may be positioned in or near the opening of a second of two conventional fluid collection containers 104, such that the collected sweat is directed from the sweat outlet port 97B into the collection container 104 (see the arrow A3). Upon extraction of all the collected sweat in the sweat collection device 80, the collection containers 104 may be sealed for storage and subsequent processing and analysis.

Figure 6:
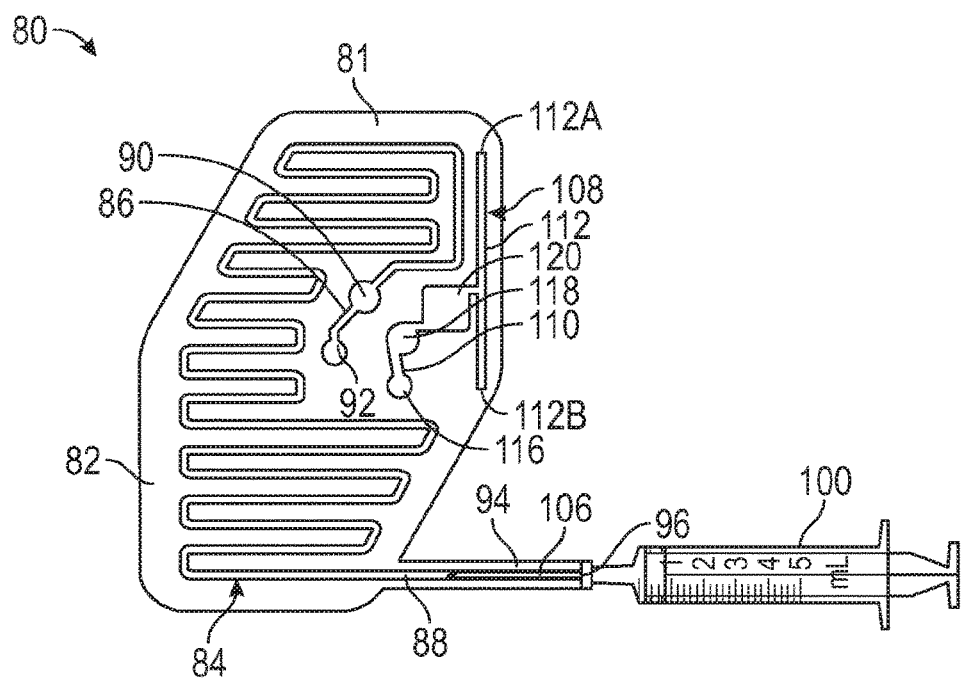
FIG. 6 is a plan view of the sweat collection device illustrated in FIG. 2 through 5 and showing a second embodiment of a method of extracting a collected sample of skin bio-fluid from the sweat collection device.
Figure 7:
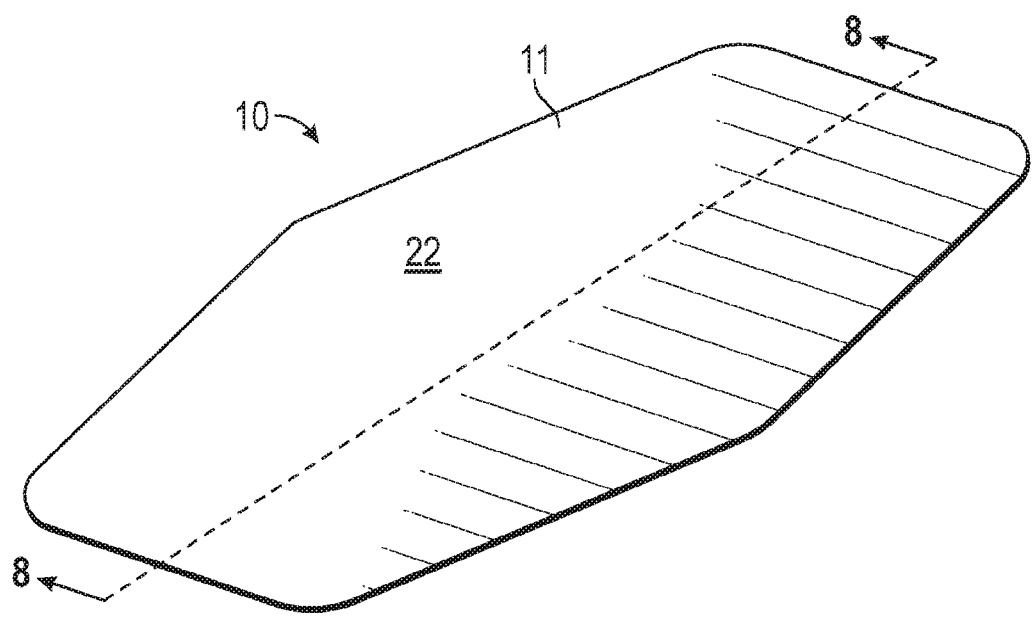
FIG. 7 is a plan view of a sweat collection device in accordance with this invention.
Figure 8:
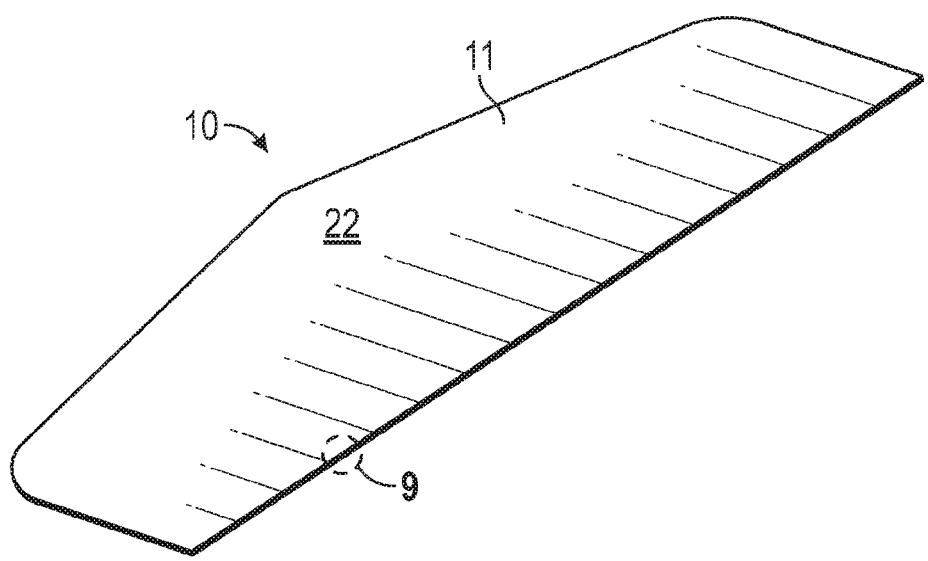
FIG. 8 is a cross-sectional view taken along the line 2-2 of FIG. 1.

Referring now to FIG. 6, a second method of extracting sweat from the sweat collection device 80 is shown wherein the collected sweat is pulled from the sweat collection device 80. As shown, a syringe 100 has needle 106 attached thereto. The needle 106 has a size corresponding to the size of the sweat outlet port 96, such as about 0.040 in (1.0 mm) Advantageously, the needle 106 is configured to be inserted into the sweat outlet port 96 to define an airtight seal. If desired, a tube (not shown, but similar to the tube 102) may be connected between the syringe 100 and the needle 106.

The operator may next pull outwardly on a plunger of the syringe 100 to produce a vacuum in a barrel of the syringe 100. This vacuum results in a pressure gradient from the sweat outlet port 96 to the barrel of the syringe 100, thus causing the sweat in the first sweat collection channel 84 to move through the needle 106 and into the barrel of the syringe 100. Upon extraction of all the collected sweat in the sweat collection device 80, the syringe 100 may be removed from the sweat collection device 80 for storage and subsequent processing and analysis.

If desired, a second sweat channel 108 may also be formed in the second, third, and fourth layers 14, 16, and 18, respectively in the same manner that the first sweat collection channel 84 is formed. The second sweat channel 108 has a sweat inlet end 110 and an elongated end portion 112 that includes first and second closed ends 112A and 112B, respectively, and unlike the first sweat collection channel 84, does not define a sweat outlet. A transverse slit 114 may be formed in the first closed end 112A of the end portion 112 to vent air as sweat moves through the second sweat channel 108. The second sweat channel 108 includes a second sweat inlet port 116 in fluid communication therewith, and may also include a first and a second biochemical assay well 118 and 120, respectively, near the sweat inlet end 110.

The sweat inlet port 116 and the biochemical assay well 118 may have any desired diameter, such as diameter of about 0.040 in and 0.160 (about 1.00 mm and 4.00 mm), respectively. Alternatively, the sweat inlet port 116 may have a diameter of about 0.040 in to about 0.100 in (about 1.00 mm to about 2.50 mm), and the first biochemical assay well 118 may have a diameter of about 0.020 in to about 0.200 in (about 0.50 mm to about 5.00 mm) In the illustrated embodiment, the second biochemical assay well 120 is substantially square and has a size of about 0.21 in×0.21 in (about 5.3 mm×5.3 mm) Alternatively, the second biochemical assay well 120 may have a size of about 0.10 in to about 0.25 in×about 0.10 in to about 0.25 in (about 2.54 mm to about 6.35 mm×about 2.54 mm to about 6.35 mm) If desired, the second sweat channel 108 may employ a two-stage assay, wherein an assay in the first biochemical assay well 118 must be first mixed with sweat before being mixed with a second assay in the second biochemical assay well 120. Regarding [095], 120 is a second assay well which can be used for a 2-stage assay. Additionally, the second sweat channel 108 may employ a multi-stage assay, wherein the second sweat channel 108 has as many stages, defined by any number of additional assay wells (not shown). For example, a glucose assay may have two or three stages, and thus two or three assay wells, depending on the specific assay chosen.

The first biochemical assay well 118 defines a colorimetric reaction site that may be configured to react with very small, such as microliter volumes of sweat. The first biochemical assay well 118 may contain colored dyes, for example conventional food coloring dyes), chemical assays, fluoroscopic dyes, enzymatic assays, heavy metal assays, and protein/DNA based assays. For example, a chemical reaction between sweat and the assay in the first biochemical assay well 118 may induce a color change in the sweat, such as to pink. Preferably, the changed color of the sweat in the second sweat channel 108 is different from the changed color of the sweat in the dye well 90 of the first sweat collection channel 84, i.e., orange in the exemplary embodiment.

If desired, the outwardly facing surface 81 of the sweat sensing device 80 may be laminated with a very thin layer of polymer (not shown), such as a 25 μm layer of PET, having indicia, such as a trademark, printed thereon. The indicia may, for example, be semi-transparent and aligned with the second biochemical assay well 120. Because the second biochemical assay well 120 will have the color of the sweat changed in the dye well 90, in this example orange, the orange color will be visible through any transparent portions of the indicia laminated to the outwardly facing surface 81.

Figure 18:
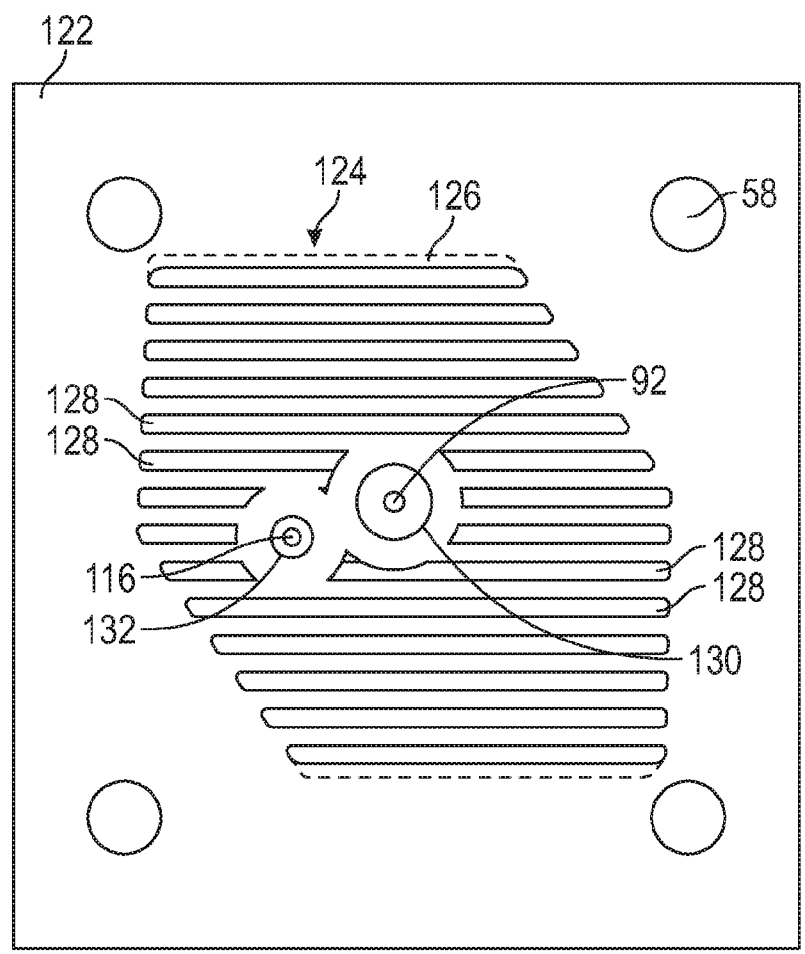
FIG. 18 a plan view of a lower surface of an assembled blank of a third embodiment of a sweat collection device in accordance with this invention.

FIG. 18 a plan view of a lower surface 126 of an assembled blank 122 of a third embodiment of a sweat collection device 124 in accordance with this invention. The sweat collection device 124 may be otherwise similar to the sweat collection device 80 and includes the first sweat inlet port 92 of the first sweat collection channel 84 (not shown in FIG. 18), and the second sweat inlet port 116 of the second sweat channel 108 (not shown in FIG. 18).

Parallel grooves 128 are formed in the surface 126 of the sweat collection device 124. Additionally, a first substantially circular depression 130 is formed in the surface 126 about the first sweat inlet port 92. Similarly, a second substantially circular depression 132 is formed in the surface 126 about the second sweat inlet port 116. The non-grooved portions of the surface 126 includes adhesive for attachment to the skin.

The grooves 128 may have a width of about 0.08 in (2 mm) Alternatively, the grooves 128 may have a width within the range of about 0.04 in to about 0.16 in (about 1.0 mm to about 4.0 mm).

The first substantially circular depression 130 may have any desired diameter, such as diameter of about 0.280 in (7.0 mm) Alternatively, the first substantially circular depression 130 may have a diameter within the range of about 0.08 in to about 0.50 in (about 2 mm to about 12.5 mm) Similarly, the second substantially circular depression 132 may have any desired diameter, such as diameter of about 0.160 in (4.0 mm) Alternatively, the second substantially circular depression 132 may have a diameter within the range of about 0.08 in to about 0.5 in (about 2 mm to about 12.5 mm) It will be understood that if desired, the first substantially circular depression 130 and the second substantially circular depression 132 may have the same diameter.

When the sweat collection device 124 is affixed to the skin of a person, only sweat from within the a first and second substantially circular depressions 130 and 132 can flow into the first and second sweat inlet ports 92 and 116, respectively. Additionally, the grooves 128 define a space between the skin and the sweat collection device 124. The grooves 128 thus provides a path for air to flow, and allows sweat to flow away from the first sweat inlet port 92 and the second sweat inlet port 116. This pattern of grooves 128 and adhesive on the surface 126 allows sweat to be collected only from a specific and predetermined area of skin.

Advantageously, allowing the sweat to flow away from the sweat inlet ports 92 and 116 allows for a precision sweat rate measurement to be obtained while allowing undesirable sweat to flow away. Sweat collected using the sweat collection device 124 can be analyzed in a skin location-specific context. For example, sweat volume may be extrapolated from a known skin surface area to estimate a volume of whole body sweat loss. For example, the sweat collection device 124 is configured to facilitate sweat collection from sweat pores within an area of interest, i.e., within the first and second substantially circular depressions 130 and 132. Sweat from other, undesirable sweat pores distributed throughout the adhesive surface 126 flow along the parallel grooves 128 and prevent ingress into the sweat inlet ports 92 and 116. This undesirable sweat is effectively wicked away from the sweat inlet ports 92 and 116 and toward the periphery of the sweat collection device 124, preventing it from being measured.

Figure 20:
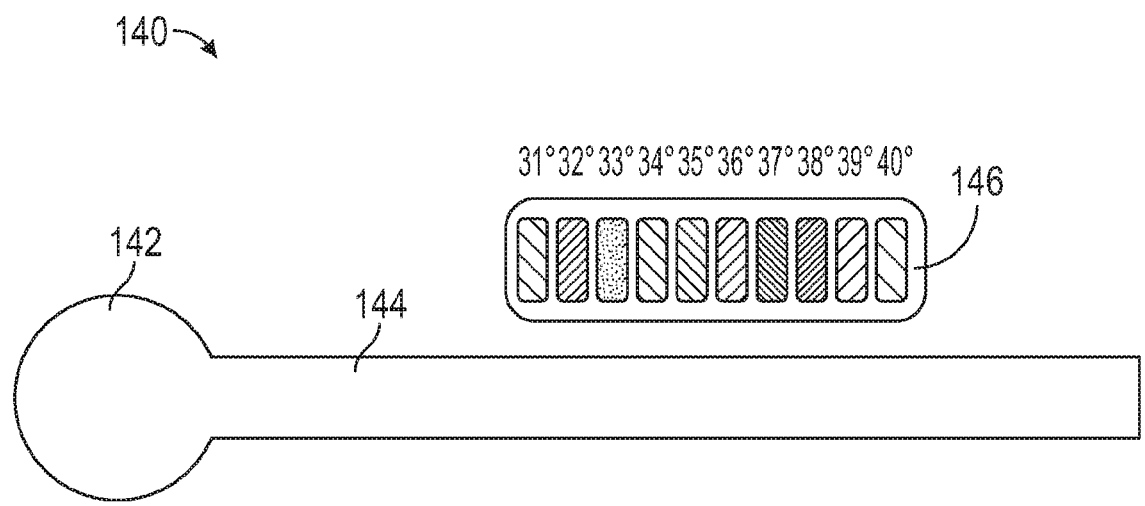
FIG. 20 is an enlarged plan view of a thermo-chromatic temperature indicator than may be used with any embodiment of the sweat collection device illustrated herein.

Referring now to FIG. 20, any of the sweat collection devices disclosed herein may include the temperature sensing channel 140 configured to measure temperature. The temperature channel 140 includes a sweat inlet port 142 that extends through the lower layer 20, described above, and is in fluid communication with a sweat channel 144.

In the illustrated embodiment, encapsulated thermochromic ink that is tuned to measure temperature may be deposited within the sweat channel 144. Examples of suitable thermochromic inks include, but are not limited to, inks having cholesteric and chiral nematic structures. The ink may be deposited directly between laminating layers of the sweat collection device, such as between the second layer 14 and the fourth layer 18 as shown in FIG. 12, or between the first layer 12 and the fifth layer 20 in embodiment without the second layer 14 and the fourth layer 18. Alternatively, the temperature sensing channel 140 may be formed in a pre-assembled, modular strip (not shown) and attached to any of the sweat collection devices disclosed herein.

Alternatively, the temperature sensing channel 140 may include one or more assay wells (not shown). Different formulations of the encapsulated thermochromic ink that transition at successively increasing temperature may be deposited in the assay wells (not shown). An outwardly facing surface of the sweat collection device may also include human or machine-readable markings that can change color at a predetermined temperature, thus indicating when the sweat collection device is operating at that specific temperature. This form of temperature sensing and control could be used to monitor a collected sweat sample to ensure that it remains in a temperature range required for sample viability and required for benchtop lab based testing. If the sweat collection device exceeds a predetermined temperature range, the sweat extracted therefrom may be deemed contaminated and unusable.

The thermochromic ink will change color as the sweat temperature is increased, for example from colorless to red, orange, yellow, green, blue, and violet. Alternatively, a thermochromic ink may be selected that is temperature insensitive and will thus change color only at a pre-determined specific transition temperature. With such a temperature insensitive ink, when the sweat collection device reaches the transition temperature, the thermochromic ink changes color.

The temperature channel 140 may also include an adjacent temperature indicator 146 that assigns a temperature value to a color as may appear in the sweat channel 144. Advantageously, the encapsulated thermochromic ink may be tuned to measure skin temperatures and used to extrapolate core body temperature.

Additionally, and if desired, a pH sensor (not shown) may be used adjacent to a sweat collection channel, such as the first sweat collection channel 84, to indicate a pH value and to serve as a validating measurement during sweat collection. If pH levels are abnormal, for example undesirably high, this could indicate sweat samples that are contaminated by bacteria or other foreign substances. This information is valuable in embodiments wherein sweat is stored in the sweat collection device for long periods of time using the occlusion tabs 98. Such a pH sensor may thus serve as a simple visual indicator of the viability of the sweat sample before extraction and analysis are initiated.

It will be understood that in addition to the uses described herein above, the various embodiments of the sweat collection devices disclosed herein may be used in other ways. For example, the sweat collection device 80 may form part of a bandage or other wound covering. The sweat inlet port 92 of the inlet port 92 of the sweat collection device 80 may then be placed over a wound to capture wound exudate rather than sweat. Although collecting and storing wound exudate rather than sweat, the sweat collection device 80 may be used as described above, and the wound exudate may be collected, stored, shipped, and analyzed as described above. The wound data monitored and collected may be used to assess the nature and progress of wound healing, the presence and extent of infection, and other medically relevant factors. Wound exudate collected and extracted from the sweat collection device 80 may be analyzed using conventional methods to detect biomarkers, identify bacterial strains, and the like.

Additionally, the sweat collection device 80 may be placed over a region of skin coated with an exogenous topical lotion, fragrance, and/or antiperspirant, including but not limited to sunscreen lotion and hydration cream. The sweat collection device 80 may be used to collect sweat from these coated skin regions, and further used to characterize the effect of these exogenous topical lotions and the chemicals therein on pH levels, and on local average and instantaneous sweat rates. When used in this way, the sweat collection device 80 may be attached to any part of the body, including but not limited to the forearms, the lower back, palm of the hand, and the upper bicep, and may be used to measure local instantaneous sweat rates during physical activity or under at-rest conditions when affixed over an exogenous topical lotion, such as topical sunscreen lotion.

Any measurements taken with the sweat collection device 80 may be used, for example, to evaluate the effect of various sunscreens on the production of sweat by the eccrine system.

Further, the sweat collection device 80 may be placed near the apocrine glands to characterize the effect of antiperspirants, medical topical creams, such as those used to regulate perspiration (e.g. hyperhidrosis), and topical fragrance creams and liquids on apocrine average and instantaneous sweat rates.

Also, the sweat collection device 80 may be placed near a transdermal drug patch, such as a nicotine patch, a transdermal drug delivery apparatus, such as a continuous glucose monitoring device, or a sub-dermal implant, such as a Medtronic Reveal LINQ™ cardiac monitoring device, to evaluate the effects of these patches, implants, and devices on average and instantaneous sweat rate. If desired, a near-field communication (NFC) chip may be mounted on the sweat collection device 80 and configured to receive information from non-invasive or medical implants to correlate the status of these patches, implants, or devices relative to sweat rate measurements.

It will be further understood that the various embodiments of the sweat collection devices disclosed herein may be used on one or more people and may be monitored remotely by one or more associated wearable sweat collection systems. Each wearable sweat collection device may capture a volume of sweat and may also indicate the total sweat volume captured, the temperature, and/or the pH levels from one or more locations on the body. The wearable sweat collection devices may be monitored and read by visual inspection, or with images taken with a smartphone. Once the collected volume of sweat surpasses a minimum target volume, such as 10 µL of collected sweat, the collected sweat may be extracted as described above. The extracted sweat may be immediately processed and analyzed, or may be stored for later analysis.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A sweat collection device comprising:
    a flexible body having a first, outwardly facing surface and a second, skin-facing surface; and
    a sweat collection channel formed in the body, the sweat collection channel having a first end defining a sweat inlet port, and a second end defining a sweat outlet port;
    wherein the sweat inlet port and the sweat outlet port are configured to be closed and sealed such that the sweat collection device and the collected sweat therein may be stored and shipped; and
    wherein the skin-facing surface further includes a plurality of parallel grooves formed therein, each groove defining a space between the skin of a person to whom the sweat collection device has been affixed and the sweat collection device, the spaces providing a path for air to flow, and a path for sweat to flow away from the sweat inlet port and the second sweat inlet port.

2. The sweat collection device according to claim 1, further including a first occlusion tab affixed to the sweat inlet port and a second occlusion tab affixed to the sweat outlet port after a desired volume of sweat has been collected in the sweat collection device, the first and second occlusion tabs defining fluid-tight seals of the sweat inlet port and the sweat outlet port, respectively.

3. The sweat collection device according to claim 1, further including a flexible fluidics tail defining an outlet member at the second end of the sweat collection channel and defining the sweat outlet port at a distal end thereof, the outlet member extending outwardly from a peripheral edge of the flexible body, and the sweat collection channel extending through the outlet member to the sweat outlet port.

4. The sweat collection device according to claim 1, wherein the skin-facing surface further includes a substantially circular depression formed therein about the sweat inlet port, wherein when the sweat collection device is affixed to the skin of a person, only sweat from within the substantially circular depression can flow into the sweat inlet port.

5. The sweat collection device according to claim 1, further including:
    a biochemical assay well formed in the sweat collection channel; and
    a dye disposed in the biochemical assay well, wherein the dye is an uncharged and non-reactive dye chosen to contain none of the chemicals to be detected in the sweat collected in the sweat collection device.

6. The sweat collection device according to claim 1, wherein the outlet member includes a longitudinally extending first portion and a longitudinally extending second portion that is in fluid communication with the first portion and extends transversely therefrom, wherein the first portion defines a first sweat outlet port and the second portion defines a second sweat outlet port.

7. A sweat collection device comprising:
    a flexible body having a first, outwardly facing surface and a second, skin-facing surface; and
    a sweat collection channel formed in the body, the sweat collection channel having a first end defining a sweat inlet port, and a second end defining a sweat outlet port;
    wherein the sweat inlet port and the sweat outlet port are configured to be closed and sealed such that the sweat collection device and the collected sweat therein may be stored and shipped; and
    wherein the sweat collection channel is a first sweat collection channel, the sweat collection device further including a second sweat collection channel having a sweat inlet end and an elongated end portion that includes first and second closed ends, a transverse slit formed in one of the first closed end and the second closed end configured to vent air as sweat moves through the second sweat channel, and a biochemical assay well near the sweat inlet end, the biochemical assay well having an assay material deposited therein.

8. The sweat collection device according to claim 7, wherein the assay material is chosen to detect one of a physiologic and a biometric condition in the sweat in the second sweat collection channel, the physiologic and biometric conditions selected from the group consisting of sweat volume, sweat volume loss, sweat rate, sweat chloride loss, sweat sodium loss, sweat lactate loss, sweat electrolyte loss, sweat metabolite loss, sweat pH, sweat glucose, and foreign chemical and toxin concentrations in the sweat.

9. The sweat collection device according to claim 7, wherein the outwardly facing surface of the sweat collection device includes visual landmarks indicating a volume of fluid that corresponds to the visible fluid progression through the sweat collection channel, and wherein the visual landmarks are configured to be read by an operator and by a camera.

10. The sweat collection device according to claim 1, wherein the sweat collection channel is a first sweat collection channel, the sweat collection device further including a second sweat collection channel, wherein the second sweat collection channel is one of a temperature sensing channel configured to measure temperature and a pH sensor channel and configured to provide information about a state of the collected sweat sample while the sweat collection device is kept in storage, and wherein the temperature sensing channel includes a sweat inlet port in fluid communication with a sweat channel, and an encapsulated thermochromic ink that is tuned to measure temperature deposited within the sweat channel.

11. The sweat collection device according to claim 1, further including:
- a biochemical assay well formed in the sweat collection channel; and
- a dye disposed in the biochemical assay well, the dye positioned to react with sweat traveling through the sweat collection channel and to provide one of a visual indicator and an indicator detectable by a camera and connected processor of the flow of the sweat in the sweat collection channel.

* * * * *

UNITED STATES PATENT AND TRADEMARK OFFICE
CERTIFICATE OF CORRECTION

| | |
|---|---|
| PATENT NO. | : 11,337,681 B2 |
| APPLICATION NO. | : 16/758590 |
| DATED | : May 24, 2022 |
| INVENTOR(S) | : Jeffrey B. Model et al. |

It is certified that error appears in the above-identified patent and that said Letters Patent is hereby corrected as shown below:

In the Claims

Claim 1, Column 17, Line 60, the phrase:
"the second sweat inlet port."
Should be changed to:
--the sweat outlet port.--

Signed and Sealed this
Thirtieth Day of July, 2024

Katherine Kelly Vidal
*Director of the United States Patent and Trademark Office*